United States Patent
Angibaud et al.

(10) Patent No.: US 7,153,958 B2
(45) Date of Patent: Dec. 26, 2006

(54) FARNESYL TRANSFERASE INHIBITING BENZOHETEROCYCLIC DERIVATIVES

(75) Inventors: Patrick René Angibaud, Fontaine-Bellenger (FR); Marc Gaston Venet, Le Mesnil-Esnard (FR); Virginie Sophie Poncelet, Le Manoir sur Seine (FR)

(73) Assignee: Janssen Pharmaceutica N.V., Beerse (BE)

( * ) Notice: Subject to any disclaimer, the term of this patent is extended or adjusted under 35 U.S.C. 154(b) by 358 days.

(21) Appl. No.: 10/432,292

(22) PCT Filed: Nov. 15, 2001

(86) PCT No.: PCT/EP01/13317

§ 371 (c)(1),
(2), (4) Date: May 19, 2003

(87) PCT Pub. No.: WO02/42296

PCT Pub. Date: May 30, 2002

(65) Prior Publication Data

US 2004/0034218 A1    Feb. 19, 2004

(30) Foreign Application Priority Data

Nov. 21, 2000   (EP) .................... 00204149

(51) Int. Cl.
*C07D 223/00*   (2006.01)
*C07D 487/02*   (2006.01)

(52) U.S. Cl. ............. 540/484; 540/492; 540/567; 540/611

(58) Field of Classification Search ........... 540/484, 540/492, 567, 611; 514/212.01, 218, 213.01
See application file for complete search history.

(56) References Cited

U.S. PATENT DOCUMENTS

| 3,682,892 A | 8/1972 | Ning et al. |
| 5,116,971 A | 5/1992 | Harreus et al. |

FOREIGN PATENT DOCUMENTS

| EP | 0317564 B1 | 7/1995 |
| GB | 1435981 | 5/1976 |
| WO | WO 96/20184 A1 | 7/1996 |
| WO | WO 97/16443 A1 | 5/1997 |
| WO | WO 97/21701 A1 | 6/1997 |
| WO | WO 98/40383 A1 | 9/1998 |
| WO | WO 98/49157 A1 | 11/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |
| WO | WO 01/53289 A1 | 7/2001 |

OTHER PUBLICATIONS

Kohl et al., "Selective Inhibition of ras-Dependent Transformation by a Farnesyltransferase Inhibitor," *Science*, 1993, pp. 1934-1937, vol. 260, No. 5116.

Rak et al., " Mutant ras Oncogenes Upregulate VEGF/VPF Expression: Implications for Induction and Inhibition of Tumor Angiogenesis," *Cancer Research*, 1995, pp. 4575-4580, vol. 55, No. 20.

PCT International Search Report for PCT Appln. No. PCT/EP01/13317, mailed Feb. 5, 2002 which relates to this corresponding U.S. Application, filed herewith.

*Primary Examiner*—James O. Wilson
*Assistant Examiner*—Paul V. Ward

(57) ABSTRACT

This invention comprises the novel compounds of formula (I)

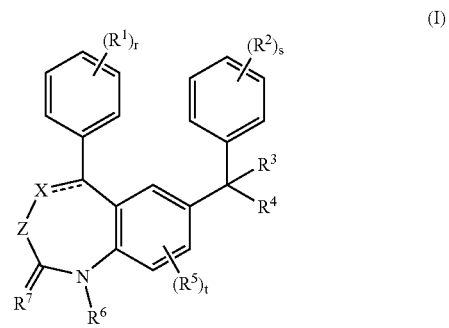

wherein r, s, t, X, Z, $R^1$, $R^2$, $R^3$, $R^4$, $R^5$, $R^6$ and $R^7$ have defined meanings, having farnesyl transferase inhibiting activity; their preparation, compositions containing them and their use as a medicine.

36 Claims, No Drawings

FARNESYL TRANSFERASE INHIBITING BENZOHETEROCYCLIC DERIVATIVES

CROSS REFERENCE TO RELATED APPLICATIONS

This application is the national stage of Application No. PCT/EP01/13317, filed Nov. 15, 2001 which application claims priority from EP 00204149.9 filed Nov. 21, 2000.

The present invention is concerned with novel benzoheterocyclic derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., *Science*, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolone derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolone compounds having farnesyl transferase inhibiting activity are described in WO 00/12498, 00/12499, 00/47574 and 01/53289.

Unexpectedly, it has been found that the present novel benzoheterocyclic compounds show farnesyl protein transferase inhibiting activity.

The present invention concerns compounds of formula (I):

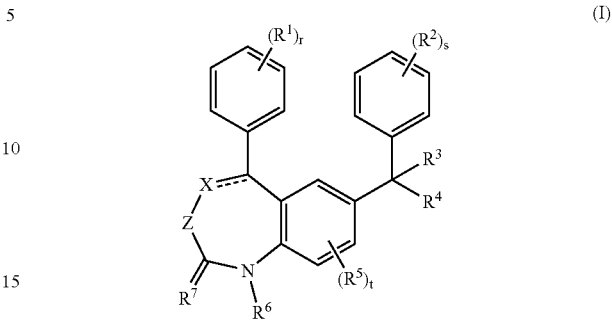

or a pharmaceutically acceptable salt or N-oxide or stereochemically isomeric form thereof, wherein the dotted line represents an optional bond;

r and s are each independently 0, 1, 2, 3, 4 or 5;

t is 0, 1, 2 or 3;

X is —NH—, —O—, or —S— (when the optional bond represented by the dotted line is absent) or —N═ (when the optional bond represented by the dotted line is present);

Z is $C_{1-2}$ alkanediyl which may be optionally substituted by one or more substituents independently selected from $C_{1-4}$alkyl (optionally substituted by hydroxy), aryl $C_{1-4}$alkyl, $C_{1-4}$alkyloxy$C_{1-4}$alkyl, hydroxy$C_{1-4}$alkyl, amino$C_{1-4}$alkyl, mono or dialkylamino$C_{1-4}$alkyl, $C_{1-4}$alkylthio$C_{1-4}$alkyl or aryl;

each $R^1$ and $R^2$ is independently azido, hydroxy, halo, cyano, nitro, $C_{1-6}$alkyl, —$(CR^{20}R^{21})_p$—$C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}S$ $C_{1-6}$alkyl, trihalomethyl, aryl$C_{1-6}$alkyl, Het$^2$$C_{1-6}$alkyl, —$C_{1-6}$alkyl-NR$^{22}$R$^{23}$, —$C_{1-6}$alkylNR$^{22}$$C_{1-6}$alkyl-NR$^{22}$R$^{23}$, —$C_{1-6}$alkylNR$^{22}$-Het$^2$, —$C_{1-6}$alkylNR$^{22}$—$C_{1-6}$alkyloxy$C_{1-6}$alkyl, —$C_{1-6}$alkylNR$^{22}$—$C_{1-6}$alkyl-S— $C_{1-6}$alkyl-Ar$^2$, —$C_{1-6}$alkylNR$^{22}$—$C_{1-6}$alkyl-S—$C_{1-6}$ alkyl, —$C_{1-6}$alkylNR$^{22}$$C_{1-6}$alkyl-Ar$^2$ (in which the $C_{1-6}$alkyl moiety adjacent to the Ar$^2$ is optionally substituted by $C_{1-6}$alkyloxycarbonyl), —$C_{1-6}$alkylNR$^{22}$$C_{1-6}$ alkyl-Het$^2$, —$C_{1-6}$alkylNR$^{22}$COC$_{1-6}$alkyl, —$C_{1-6}$ alkylNR$^{22}$COAlkAr$^2$, —$C_{1-6}$alkylNR$^{22}$COAr$^2$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, —OC$_{1-6}$alkyl-NR$^{22}$R$^{23}$, trihalomethoxy, aryl$C_{1-6}$alkyloxy, Het$^2$$C_{1-6}$alkyloxy, $C_{1-6}$alkylthio, $C_{2-6}$alkenyl, cyano$C_{2-6}$alkenyl, —$C_{2-6}$alkenyl-NR$^{22}$R$^{23}$, hydroxycarbonyl$C_{2-6}$alkenyl, $C_{1-6}$alkyloxycarbonyl$C_{2-6}$alkenyl, $C_{2-6}$alkynyl, —CHO, $C_{1-6}$alkylcarbonyl, hydroxy$C_{1-6}$ alkylcarbonyl, hydroxycarbonyl, $C_{1-6}$alkyloxycarbonyl, —CONR$^{22}$R$^{23}$, —CONR$^{22}$—$C_{1-6}$alkyl-NR$^{22}$R$^{23}$, —CONR$^{22}$—$C_{1-6}$alkyl-Het$^2$, —CONR$^{22}$—$C_{1-6}$alkyl-Ar$^2$, —CONR$^{22}$-Het$^2$, —CONR$^{22}$Ar$^2$, —CONR$^{22}$—O— $C_{1-6}$alkyl, —CONR$^{22}$—$C_{1-6}$alkenyl, —NR$^{22}$R$^{23}$, —OC(O)R$^{24}$, —CR$^{24}$═NR$^{25}$, —CR$^{24}$═N—OR$^{25}$, —NR$^{24}$C (O)NR$^{22}$R$^{23}$, —NR$^{24}$SO$_2$R$^{25}$, —NR$^{24}$C(O)R$^{25}$, —S(O)$_{0-2}$R$^{24}$, —SO$_2$NR$^{24}$R$^{25}$, —C(NR$^{26}$R$^{27}$)═NR$^{28}$; —Sn(R$^{24}$)$_3$, —SiR$^{24}$R$^{24}$R$^{25}$, —B(OR$^{24}$)$_2$, —P(O) OR$^{24}$OR$^{25}$, Ar$^2$oxy, Het$^2$-oxy, or a group of formula -Z, —CO-Z or —CO—NR$^y$-Z in which $R^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, —COOR$^{24}$, aminocarbonyl, $C_{1-6}$alkylthio, hydroxy, —NR$^{22}$R$^{23}$, $C_{1-6}$alkylsulphonylamino, $C_{1-6}$alkyl, haloC$_{1-6}$alkyl, $C_{1-6}$alkyloxy or phenyl; or two $R^1$ or $R^2$ substituents adjacent to one another on the phenyl ring may form together a bivalent radical of formula —O—CH$_2$—O— (a-1)

—O—CH$_2$—CH$_2$—O— (a-2)

—O—CH═CH— (a-3)

—O—CH$_2$—CH$_2$— (a4)

—O—CH$_2$—CH$_2$—CH$_2$— (a-5)

—CH═CH—CH═CH— (a-6)

p is 0 to 5;

$R^{20}$ and $R^{21}$ are independently hydrogen or $C_{1-6}$ alkyl and are independently defined for each iteration of p in excess of 1;

$R^{22}$ and $R^{23}$ are independently hydrogen, $C_{1-6}$ alkyl or —(CR$^{20}$R$^{21}$)$_p$—C$_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, haloC$_{1-6}$alkyl, $C_{1-6}$alkyloxy, OCF$_3$, hydroxycarbonyl, $C_{1-6}$alkyloxycarbonyl, aminocarbonyl, mono- or di-(C$_{1-6}$alkyl)aminocarbonyl, amino, mono- or di(C$_{1-6}$alkyl)amino, $C_{1-6}$alkylsulfonylamino, oxime, or phenyl;

$R^{24}$ and $R^{25}$ are independently hydrogen, $C_{1-6}$ alkyl, —CR$_{20}$R$_{21}$)p-C$_{3-10}$cycloalkyl or arylC$_{1-6}$alkyl;

$R^{26}$, $R^{27}$ and $R^{28}$ are independently hydrogen and $C_{1-6}$alkyl or C(O) $C_{1-6}$alkyl;

$R^3$ is hydrogen, halo, cyano, $C_{1-6}$alkyl, —(CR$^{20}$R$^{21}$)$_p$—$C_{3-10}$cycloalkyl, haloC$_{1-6}$alkyl, cyanoC$_{1-6}$alkyl, hydroxyC$_{1-6}$alkyl, $C_{1-6}$alkyloxyC$_{1-6}$alkyl, arylC$_{1-6}$alkyloxyC$_{1-6}$alkyl, $C_{1-6}$alkylthioC$_{1-6}$alkyl, hydroxycarbonylC$_{1-6}$alkyl, $C_{1-6}$alkylcarbonylC$_{1-6}$alkyl, $C_{1-6}$alkyloxycarbonylC$_{1-6}$alkyl, —C$_{1-6}$alkyl-NR$^{22}$R$^{23}$, —C$_{1-6}$alkyl-CONR$^{22}$R$^{23}$, arylC$_{1-6}$alkyl, Het$^2$C$_{1-6}$alkyl, C$_{2-6}$alkenyl, —C$_{2-6}$alkenyl NR$^{22}$R$^{23}$, $C_{2-6}$alkynyl, hydroxycarbonyl, $C_{1-6}$alkyloxycarbonyl, aryl, or Het$^2$; or a radical of formula —O—R$^{10}$ (b-1)

—S—R$^{10}$ (b-2)

—NR$^{11}$R$^{12}$ (b-3)

or

—N═CR$^{10}$R$^{11}$ (b-4)

wherein $R^{10}$ is hydrogen, $C_{1-6}$alkyl, —(CR$^{20}$R$^{21}$)$_p$—C$_{3-10}$cycloalkyl, arylC$_{1-6}$alkyl, C$_{2-6}$alkenyl, C$_{2-6}$alkynyl, $C_{1-6}$alkylcarbonyl, aryl, a group of formula —NR$^{22}$R$^{23}$R or —C$_{1-6}$alkylC(O)OC$_{1-6}$alkyl NR$^{22}$R$^{23}$, or a radical of formula -Alk-OR$^{13}$ or -Alk-NR$^{14}$R$^{15}$;

$R^{11}$ is hydrogen, $C_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl;

$R^{12}$ is hydrogen, hydroxy, $C_{1-6}$alkyl, —(CR$^{20}$R$^{21}$)$_p$—C$_{3-10}$cycloalkyl, $C_{1-6}$alkylcarbonylC$_{1-6}$alkyl, arylC$_{1-6}$alkyl,C$_{2-6}$alkenyl, C$_{2-6}$alkynyl, aryl, $C_{1-6}$alkyloxy, a group of formula —NR$^{22}$R$^{23}$, $C_{1-6}$alkylcarbonylamino, $C_{1-6}$alkylcarbonyl, haloC$_{1-6}$alkylcarbonyl, arylC$_{1-6}$alkylcarbonyl, Het$^2$C$_{1-6}$alkylcarbonyl, arylcarbonyl, $C_{1-6}$alkyloxycarbonyl, trihaloC$_{1-6}$alkyloxycarbonyl, $C_{1-6}$alkyloxyC$_{1-6}$alkylcarbonyl, aminocarbonyl, mono- or di(C$_{1-6}$alkyl)aminocarbonyl wherein the alkyl moiety may optionally be substituted by one or more substituents independently selected from aryl and $C_{1-6}$alkyloxycarbonyl substituents; aminocarbonylcarbonyl, mono- or di(C$_{1-6}$alkyl)aminoC$_{1-6}$alkylcarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl, —(CR$^{20}$R$^{21}$)$_p$—C$_{3-10}$cycloalkyl, C$_{2-6}$alkenyl, C$_{2-6}$alkynyl, $C_{1-6}$alkylcarbonyl, hydroxyC$_{1-6}$alkyl, aryl or arylC$_{1-6}$alkyl;

$R^{14}$ is hydrogen, $C_{1-6}$alkyl, —(CR$^{20}$R$^{21}$)$_p$—C$_{3-10}$cycloalkyl, C$_{2-6}$alkenyl, C$_{2-6}$alkynyl, aryl or arylC$_{1-6}$alkyl; $R^{15}$ is hydrogen, $C_{1-6}$alkyl, —(CR$^{20}$R$^{21}$)$_p$—C$_{3-10}$cycloalkyl, C$_{2-6}$alkenyl, C$_{2-6}$alkynyl, $C_{1-6}$alkylcarbonyl, aryl or arylC$_{1-6}$alkyl;

$R^4$ is a radical of formula

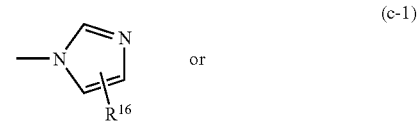

(c-1)

or

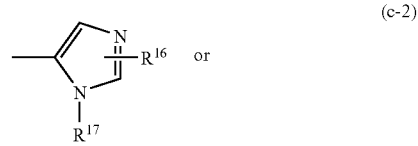

(c-2)

or

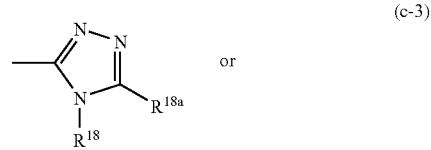

(c-3)

or

(c-4)

wherein $R^{16}$ is hydrogen, halo, $C_{1-6}$alkyl, —(CR$^{20}$R$^{21}$)$_p$—C$_{3-10}$cycloalkyl, hydroxyC$_{1-6}$alkyl, $C_{1-6}$alkyloxyC$_{1-6}$alkyl, $C_{1-6}$alkylS(O)$_{0-2}$C$_{1-6}$alkyl, $C_{1-6}$alkyloxy, $C_{1-6}$alkylthio, a group of formula —NR$^{22}$R$^{23}$, hydroxycarbonyl, $C_{1-6}$alkyloxycarbonyl or aryl, $R^{17}$ is hydrogen, $C_{1-6}$alkyl, —(CR$^{20}$R$^{21}$)$_p$—C$_{3-10}$cycloalkyl, hydroxyC$_{1-6}$alkyl, $C_{1-6}$alkyloxyC$_{1-6}$alkyl, aryl $C_{1-6}$alkyl, trifluoromethyl, trifluoromethylC$_{1-6}$alkyl, hydroxycarbonylC$_{1-6}$alkyl, $C_{1-6}$alkyloxycarbonylC$_{1-6}$alkyl, mono- or di(C$_{1-6}$alkyl)aminosulphonyl or —C$_{1-6}$alkyl P(O)OR$^{24}$OR$^{25}$;

$R^{18}$ is hydrogen, $C_{1-6}$alkyl, —(CR$^{20}$R$^{21}$)$_p$—C$_{3-10}$cycloalkyl, arylC$_{1-6}$alkyl or $C_{1-6}$alkyloxyC$_{1-6}$alkyl;

$R^{18a}$ is hydrogen, —SH or —SC$_{1-4}$alkyl;

$R^5$ is cyano, hydroxy, halo, $C_{1-6}$alkyl, $—(CR^{20}R^{21})_p—C_{3-10}$ cycloalkyl, $C_{2-6}$alkenyl, $C_{2-6}$alkynyl, $C_{1-6}$alkyloxy, aryl$C_{1-6}$alkyloxy, Het$^2C_{1-6}$alkyloxy, hydroxycarbonyl, $C_{1-6}$alkyloxycarbonyl, or a group of formula $—NR^{22}R^{23}$ or $—CONR^{22}R^{23}$.

$R^6$ is hydrogen, $C_{1-6}$alkyl, $—CF_3$, $—(CR^{20}R^{21})_p—C_{3-10}$cycloalkyl, cyano$C_{1-6}$alkyl, $—C_{1-6}$alkylCO$_2R^{24}$, aminocarbonyl$C_{1-6}$alkyl or $—C_{1-6}$alkyl-$NR^{22}R^{23}$, $R^{24}SO_2$, $R^{24}SO_2C_{1-6}$alkyl, $—C_{1-6}$alkyl-OR$^{24}$, $—C_{1-6}$alkyl-SR$^{24}$, $—C^{1-6}$alkylCONR$^{22}$ $—C_{1-6}$alkyl-NR$^{22}R^{23}$, $—C_{1-6}$alkyl-CONR$^{22}$—$C_{1-6}$alkyl-Het$^2$, $—C_{1-6}$alkyl CONR$^{22}$—$C_{1-6}$alkyl-Ar$^2$, $—C_{1-6}$alkyl CONR$^{22}$-Het$^2$, $—C_{1-6}$alkyl CONR$^{22}$Ar$^2$, $—C_{1-6}$alkyl CONR$^{22}$—O—$C_{1-6}$alkyl, $—C_{1-6}$alkyl CONR$^{22}$—$C_{1-6}$alkenyl, -Alk-Ar$^2$ or -AlkHet$^2$;

$R^7$ is oxygen or sulphur; or $R^6$ and $R^7$ together form a trivalent radical of formula:

$$—CR^{30}=CR^{31}—N= \quad (x\text{-}1)$$

$$—CR^{30}=N—N= \quad (x\text{-}2)$$

$$—C(=O)—NH—N= \quad (x\text{-}3)$$

$$—N=N—N= \quad (x\text{-}4)$$

$$—N=CR^{30}—N= \quad (x\text{-}5)$$

$$—CR^{30}=CR^{31}—CR^{32}= \quad (x\text{-}6)$$

$$—CR^{30}=N—CR^{31}= \quad (x\text{-}7)$$

$$—C(=O)—NH—CR^{30}= \quad (x\text{-}8)$$

$$—N=N—CR^{30}= \quad (x\text{-}9)$$

or $$—CH_2—(CH_2)_{0\text{-}1}—CH_2—N= \quad (x\text{-}10)$$

wherein each $R^{30}$, $R^{31}$ and $R^{32}$ are independently hydrogen, $C_{1-6}$ alkyl, $—OR^{24}$, $—COOR^{24}$, $—NR^{22}R^{23}$, $—C_{1-6}$ alkyl-$OR^{24}$, $—C_{1-6}$ alkylSR$^{24}$, $R^{23}R^{22}NC_{1-6}$alkyl-, $—CONR^{22}R^{23}$, $C_{2-6}$alkenyl, $C_{2-6}$alkenylAr$^2$, $C_{2-6}$alkenyl-Het$^2$, cyano, amino, thio, $C_{1-6}$ alkylthio, $—O—Ar^2$, $—S—Ar^2$ or Ar$^2$;

Ar$^2$ is phenyl, naphthyl or phenyl or naphthyl substituted by one to five substituents each independently selected from halo, hydroxy, cyano, nitro, $C_{1-6}$alkyl, halo$C_{1-6}$alkyl, -alkylNR$^{22}R^{23}$, $C_{1-6}$alkyloxy, OCF$_3$, hydroxycarbonyl, $C_{1-6}$alkyloxycarbonyl, aryloxy, $—NR^{22}R^{23}$, $C_{1-6}$alkylsulfonylamino, oxime or phenyl, or a bivalent substituent of formula $—O—CH_2—O—$ or $—O—CH_2—CH_2—O—$;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkylNR$^{22}R^{23}$, $C_{1-6}$alkyloxy, OCF$_3$, hydroxycarbonyl, $C_{1-6}$alkyloxycarbonyl, $—CONR^{22}R^{23}$, $—NR^{22}R^{23}$, $C_{1-6}$alkylsulfonylamino, oxime or phenyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfone. Aryl defines phenyl, naphthalenyl or phenyl substituted with one or more substituents each independently selected from halo, $C_{1-6}$alkyl, $C_{1-6}$alkyloxy or trifluoromethyl, cyano, hydroxycarbonyl.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (a)" is meant to include also the pharmaceutically acceptable acid addition salts and all stereoisomeric forms.

Examples of compounds of formula (a) include those wherein one or more of the following restrictions apply:
r and s are each independently 0, 1 or 2;
t is 0 or 1;
Z is $C_{1-2}$ alkanediyl;
$R^1$ is halo, $C_{1-6}$alkyl, $—(CR^{20}R^{21})_p—C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$ alkyloxy, aminoC$_{1-6}$alkyloxy, C$_{1-6}$alkylthio, hydroxycarbonyl, C$_{1-6}$alkyloxycarbonyl, —CONR$^{22}$R$^{23}$, or —CH=NOR$^{25}$; or two R$^1$ substituents adjacent to one another on the phenyl ring may independently form together a bivalent radical of formula —O—CH$_2$—O— (a-1)

—O—CH$_2$—CH$_2$—O— (a-2)

R$^2$ is halo, cyano, nitro, C$_{1-6}$alkyl, cyanoC$_{1-6}$alkyl, —C$_{1-6}$alkyl NR$^{22}$R$^{23}$; cyanoC$_{2-6}$alkenyl, —NR$^{22}$R$^{23}$, CHO, —CR$^{24}$=N—OR$^{25}$, C$_{1-6}$alkyloxycarbonyl, —CONR$^{22}$R$^{23}$; or two R$^2$ substituents adjacent to one another on the phenyl ring may independently form together a bivalent radical of formula —O—CH$_2$—O— (a-1)

—O—CH$_2$—CH$_2$—O— (a-2)

R$^3$ is hydrogen, C$_{1-6}$alkyl, —(CR$^{20}$R$^{21}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, —C$_{1-6}$alkyl NR$^{22}$R$^{23}$, Het$^2$C$_{1-6}$alkyl, —C$_{2-6}$alkenyl NR$^{22}$R$^{23}$, or -Het$^2$; or a group of formula —O—R$^{10}$ (b-1)

—NR$^{11}$R$^{12}$ (b-3)

wherein R$^{10}$ is hydrogen, C$_{1-6}$alkyl, or —(CR$^{20}$R$^{21}$)$_p$—C$_{3-10}$cycloalkyl, or a group of formula -Alk-OR$^{13}$ or -Alk-NR$^{14}$R$^{15}$;

R$^{11}$ is hydrogen or C$_{1-6}$alkyl;

R$^{12}$ is hydrogen, hydroxy, C$_{1-6}$alkyl, —(CR$^{20}$R$^{21}$)$_p$—C$_{3-10}$cycloalkyl, C$_{1-6}$alkyloxy, C$_{1-6}$alkylcarbonyl, arylC$_{1-6}$alkylcarbonyl, Het$^2$C$_{1-6}$alkylcarbonyl, aminocarbonyl, or a radical of formula -Alk-OR$^{13}$ or Alk-NR$^{14}$R$^{15}$;

wherein Alk is C$_{1-6}$alkanediyl;

R$^{13}$ is hydrogen, C$_{1-6}$alkyl or —(CR$^{20}$R$^{21}$)$_p$—C$_{3-10}$cycloalkyl;

R$^{14}$ is hydrogen, C$_{1-6}$alkyl, or —(CR$^{20}$R$^{21}$)$_p$—C$_{3-10}$cycloalkyl;

R$^{15}$ is hydrogen or C$_{1-6}$alkyl;

R$^4$ is a radical of formula (c-2) or (c-3)

wherein R$^{16}$ is hydrogen, halo or C$_{1-6}$alkyl,

R$^{17}$ is hydrogen, C$_{1-6}$alkyl, —(CR$^{20}$R$^{21}$)$_p$—C$_{3-10}$cycloalkyl, C$_{1-6}$alkyloxyC$_{1-6}$alkyl or trifluoromethyl;

R$^{18}$ is hydrogen, C$_{1-6}$alkyl or —(CR$^{20}$R$^{21}$)$_p$—C$_{3-10}$cycloalkyl;

R$^{18a}$ is hydrogen;

R$^5$ is cyano, halo, C$_{1-6}$alkyl, C$_{2-6}$alkynyl, C$_{1-6}$alkyloxy or C$_{1-6}$alkyloxycarbonyl:

R$^6$ is hydrogen, C$_{1-6}$alkyl, —C$_{1-6}$alkylCO$_2$R$^{24}$, —C$_{1-6}$alkyl-C(O)NR$^{22}$R$^{23}$, -Alk-Ar$^2$, -AlkHet$^2$ or —(CR$^{20}$R$^{21}$)$_p$—C$_{3-10}$cycloalkyl, R$^7$ is oxygen or sulphur; or R$^6$ and R$^7$ together form a trivalent radical of formula (x-1), (x-2), (x-3), (x4) or (x-9)

Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

A group of interesting compounds consists of those compounds of formula (I) wherein one or more of the following restrictions apply:

Z is C$_{1-2}$ alkanediyl;

r is 0, 1 or 2;

s is 0 or 1;

t is 0;

R$^1$ is halo, C$_{1-6}$alkyl, C$_{2-6}$alkenyl, C$_{2-6}$alkynyl or two R$^1$ substituents ortho to one another on the phenyl ring may independently form together a bivalent radical of formula (a-1);

R$^2$ is halo, cyano, nitro, CHO, —CR$^{24}$=N—OR$^{25}$ in which R$^{24}$ is hydrogen and R$^{25}$ is hydrogen or C$_{1-6}$alkyl, or two R$^2$ substituents ortho to one another on the phenyl ring may independently form together a bivalent radical of formula (a-1);

R$^3$ is Het$^2$ or a group of formula (b-1) or (b-3) wherein R$^{10}$ is hydrogen or a group of formula -Alk-OR$^{13}$. R$^{11}$ is hydrogen; R$^{12}$ is hydrogen, C$_{1-6}$alkyl, C$_{1-6}$alkylcarbonyl, hydroxy, C$_{1-6}$alkyloxy or mono- or di(C$_{1-6}$alkyl)amino-C$_{1-6}$alkylcarbonyl; Alk is C$_{1-6}$alkanediyl and R$^{13}$ is hydrogen;

R$^4$ is a group of formula (c-2) or (c-3) wherein R$^{16}$ is hydrogen, halo or C$_{1-6}$alkyl; R$^{17}$ is hydrogen or C$_{1-6}$alkyl; R$^{18}$ is hydrogen or C$_{1-6}$alkyl; R$^{18a}$ is hydrogen;

R$^6$ is hydrogen, —(CR$^{20}$R$^{21}$)$_p$—C$_{3-10}$cycloalkyl, —C$_{1-6}$alkylCO$_2$R$^{24}$, aminocarbonylC$_{1-6}$alkyl, -Alk-Ar$^2$ or -AlkHet$^2$ or C$_{1-6}$alkyl;

R$^7$ is oxygen or sulphur; or R$^6$ and R$^7$ together form a trivalent radical of formula (x-1), (x-2), (x-3), (x-4) or (x-9)

aryl is phenyl.

A particular group of compounds consists of those compounds of formula (I) wherein Z is C$_{1-2}$ alkanediyl, r is 0 or 1, s is 1, t is 0, R$^1$ is halo, C$_{1-6}$alkyl or forms a bivalent radical of formula (a-1), R$^2$ is halo, cyano or C$_{1-6}$alkyl, R$^3$ is hydrogen or a radical of formula (b-1) or (b-3), R$^{10}$ is hydrogen or -Alk-OR$^{13}$, R$^{11}$ is hydrogen and R$^{12}$ is hydrogen or C$_{1-6}$alkylcarbonyl and R$^{13}$ is hydrogen; R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen; R$^6$ is hydrogen, C$_{1-6}$alkyl, —CH$_2$—C$_{3-10}$cycloalkyl, —C$_{1-6}$alkylCO$_2$R$^{24}$ (R$^{24}$=H,Et), aminocarbonylC$_{1-6}$alkyl, -Alk-Ar or -AlkHet$^2$; R$^7$ is oxygen or sulphur; or R$^6$ and R$^7$ together form a trivalent radical of formula (x-2), (x-3), or (x-4).

More preferred compounds are those compounds of formula (I) wherein Z is C$_{1-2}$ alkanediyl, r is 0 or 1, s is 1, t is 0, R$^1$ is halo, preferably chloro and most preferably 3-chloro, R$^2$ is halo, preferably 4-chloro or 4-fluoro, or cyano, preferably 4-cyano, R$^3$ is hydrogen or a radical of formula (b-1) or (b-3), R$^9$ is hydrogen, R$^{10}$ is hydrogen, R$^{11}$ is hydrogen and R$^{12}$ is hydrogen, R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen; R$^6$ is hydrogen, C$_{1-6}$alkyl, —CH$_2$—C$_{3-10}$cycloalkyl or —C$_{1-6}$alkylAr$^2$; R$^7$ is oxygen or sulphur; or R$^6$ and R$^7$ together form a trivalent radical of formula (x-2) or (x-4).

Especially preferred compounds are those compounds of formula (I) wherein X is —S—, Z is —CH$_2$—, r and s are 1, t is 0, R$^1$ is halo, preferably chloro, and most preferably 3-chloro, R$^2$ is halo, preferably chloro, and most preferably 4-chloro, or cyano, preferably 4-cyano, R$^3$ is a radical of formula (b-1) or (b-3), R$^9$ is hydrogen, R$^{10}$ and R$^{11}$ are hydrogen and R$^{12}$ is hydrogen, R$^4$ is a radical of formula (c-2) or (c-3), wherein $R^{16}$ is hydrogen, $R^{17}$ is $C_{1-6}$alkyl preferably methyl, $R^{18}$ is $C_{1-6}$alkyl preferably methyl, $R^{18a}$ is hydrogen; $R^6$ is hydrogen, $C_{1-6}$alkyl, —$CH_2$—$C_{3-10}$cycloalkyl or -alkylAr$^2$; $R^7$ is oxygen or sulphur; or $R^6$ and $R^7$ together form a trivalent radical of formula (x-4).

The most preferred compounds according to the invention are: 5-(3-chlorophenyl)-7-[(4-chlorophenyl)hydroxy(1-methyl-1H-imidazol-5-yl)methyl]-1,5-dihydro-1-methyl-4,1-benzoxazepin-2(3H)-one, 5-(3-chlorophenyl)-7-[(4-chlorophenyl)hydroxy(1-methyl-1H-imidazol-5-yl)methyl]-1,5-dihydro-1-methyl-4,1-benzothiazepin-2(3H)-one, 5-(3chlorophenyl)-7-[(4-chlorophenyl)hydroxy(1-methyl-1H-imidazol-5-yl)methyl]-1,5-dihydro-4,1-benzoxazepine-2(3H)-thione, 7-[amino(4-chlorophenyl)(1-methyl-1H-imidazol-5-yl)methyl]-5-(3chlorophenyl)-1,5-dihydro-1-methyl-4,1-benzothiazepin-2(3H)-one, 6-(3-chlorophenyl)-α-(4-chlorophenyl)-α-(1-methyl-1H-imidazol-5-yl)-4H-tetrazolo[1,5-a][1,4]benzodiazepine-8-methanamine, 5-(3-chlorophenyl)-7-[(4-chlorophenyl)(1-methyl-1H-imidazol-5-yl)methyl]-1,5-dihydro-4,1-benzothiazepin-2(3H)-one, (B)-6-(3-chlorophenyl)-α-(4-chlorophenyl)-α-(1-methyl-1H-imidazol-5-yl)-4H,6H-tetrazolo[1,5-a][4,1]benzothiazepine-8-methanamine, 6-(3-chlorophenyl)-8-[(4-chlorophenyl)(1-methyl-1H-imidazol-5-yl)methyl]-4H,6H-tetrazolo[1,5-a][4,1]benzothiazepine, 6-(3-chlorophenyl)-8-[(4-chlorophenyl)(1-methyl-1H-imidazol-5-yl)methyl]-1,3,4,6-tetrahydro-2H-5,1-benzothiazocin-2-one and their pharmaceutically acceptable salts.

The compounds of formula (I) and their pharmaceutically acceptable salts and N-oxides and stereochemically isomeric forms thereof may be prepared in conventional manner, for example by a process which comprises:

a) cyclising a compound of formula (II):

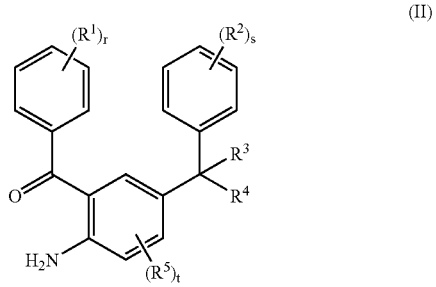

(II)

to form a compound of formula (I) in which $R^6$ is hydrogen and $R^7$ is oxygen; or b) reacting a compound of formula (III):

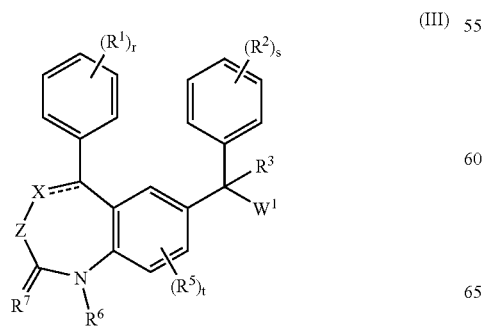

(III)

in which $W^1$ is a replaceable group, with an imidazole reagent serving to replace the group $W^1$ with an $R^4$ group of formula (c-1); or c) reacting a compound of formula (IV):

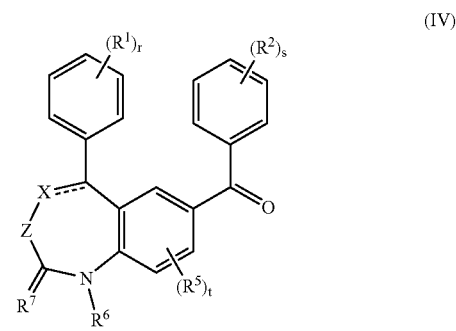

(IV)

with an imidazole reagent to form a compound of formula (I) in which $R^4$ is a group of formula (c-2), or with a 3-mercapto-4-$C_{1-6}$alkyl-1,2,4-triazole reagent to form the corresponding 3-mercapto-4-$C_{1-6}$alkyl-1,2,4-triazole derivative, which is optionally methylated to form the corresponding 3-methylmercapto derivative, and subsequently removing the 3-mercapto or 3-methylmercapto group to form a compound of formula (I) in which $R^4$ is a group of formula (c-3) in which $R^{18}$ is a $C_{1-6}$alkyl group; or with a 3-bromopyridyl reagent to form a compound of formula (I) wherein $R^4$ is a group of formula (c-4);

and optionally effecting one or more of the following conversions in any desired order:

(i) converting a compound of formula (I) into a different compound of formula (I);

(ii) converting a compound of formula (I) in to a pharmaceutically acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

With regard to process a), this can be effected for example as follows:

i) for the preparation of a compound of formula (I) in which X is —O—, a compound of formula (II) may be reacted with a reducing agent such as sodium borohydride to form a compound of formula(IIa):

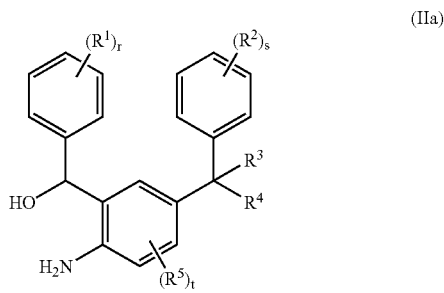

(IIa)

and the resulting compound of formula (IIa) reacted with a compound of formula (V):

in which $L^1$ and $L^2$ are halo for example bromo, the reaction being advantageously effected in an inert solvent such as $CH_2Cl_2$ in presence of a base such as aqueous potassium carbonate or triethylamine, to form a compound of formula (VI):

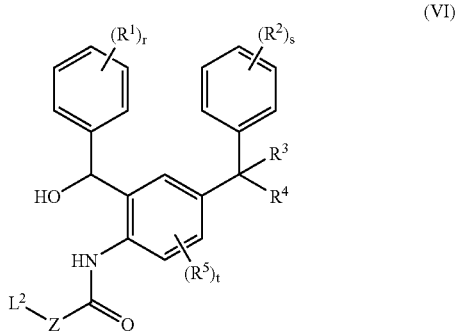

and subsequent cyclisation of the latter compound, preferably in an alcoholic solvent in a presence of a strong base such as potassium tert-butylate;

ii) for the preparation of a compound of formula (I) in which X is —S—, a compound of formula (II) may be reacted with a reducing agent such as sodium borohydride to form a compound of formula(IIa) and the resulting compound of formula (IIa) reacted with a compound of formula (VII)

preferably in an acidic media, e.g. aqueous hydrochloric acid, and at a temperature ranging from 60° C. to reflux, to form a compound of formula (VIII):

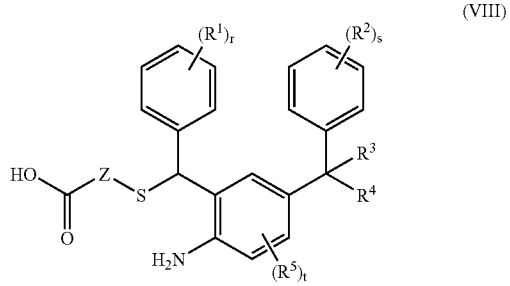

and subsequent cyclisation of the latter compound, preferably in a reaction-inert solvent such as toluene, in the presence of a dehydrating agent such as magnesium sulphate (or azeotropic removal of water) at temperatures ranging from 80° C. to reflux;

iii) for the preparation of a compound of formula (I) in which X is =N—, a compound of formula (II) may be reacted with a compound of formula (V) to form a compound of formula (VI) which is subsequently reacted with an azide for example sodium azide, preferably in a polar solvent such as methanol, at temperatures ranging from room temperature to reflux, to form a compound of formula (IX)

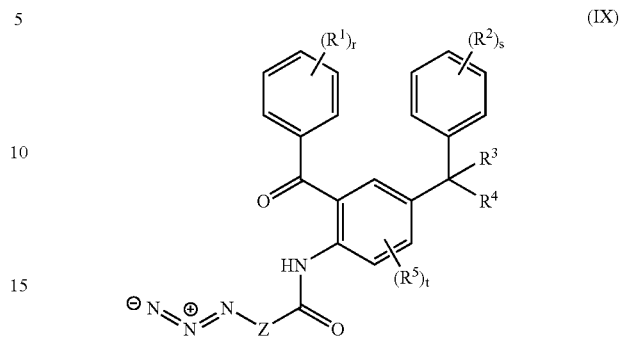

which is subsequently cyclised, preferably by hydrogenation (for example with hydrogen at 2 bars) and using Pd/C as a catalyst in a solvent such as methanol.

With regard to process b), this can be effected for example by N-alkylating an intermediate of formula (III), wherein $W^1$ is an appropriate leaving group such as, for example, chloro, bromo, methanesulfonyloxy or benzenesulfonyloxy, with an intermediate of formula (X) to form a compound of formula (I) in which $R^4$ is a group of formula (c-1) represented by compounds of formula (I-a):

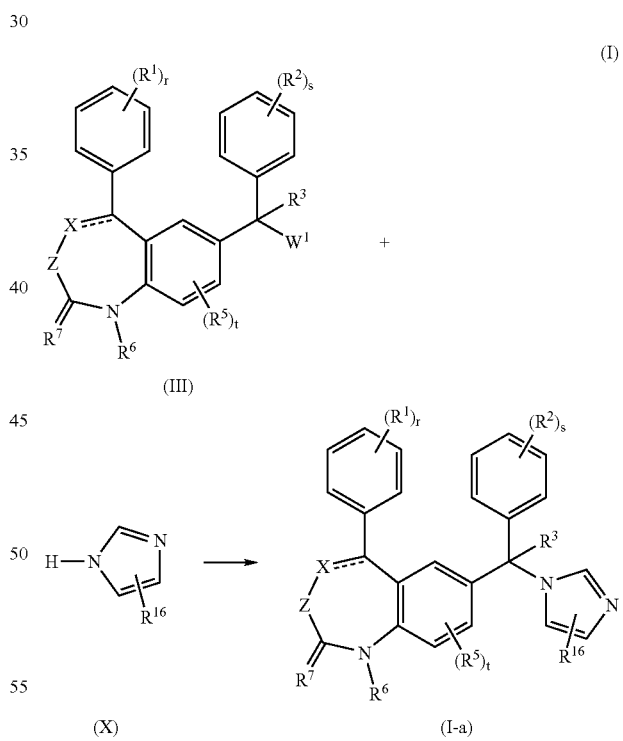

The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

Also, compounds of formula (I-a) can be prepared by reacting an intermediate of formula (IIIa) in which $W^1$ is hydroxy with an intermediate of formula (X), wherein Y is oxygen or sulfur, such as, for example, a 1,1'-carbonyldiimidazole.

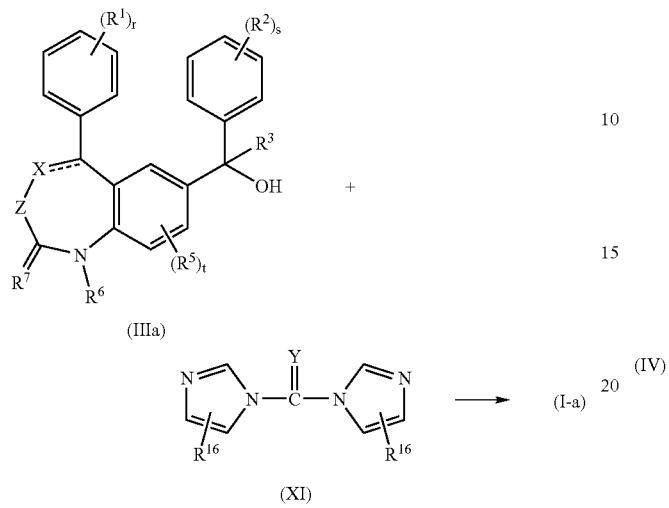

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

With regard to process c), the compounds of formula (I) wherein $R^4$ represents a radical of formula (c-2), $R^3$ is hydroxy and $R^{17}$ is $C_{1-6}$alkyl, said compounds being referred to as compounds of formula (I-b-1) may be prepared by reacting an intermediate ketone of formula (IV) with an intermediate of formula (XIIa). Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed. Other procedures with protective groups analogous to silane derivatives can also be applied.

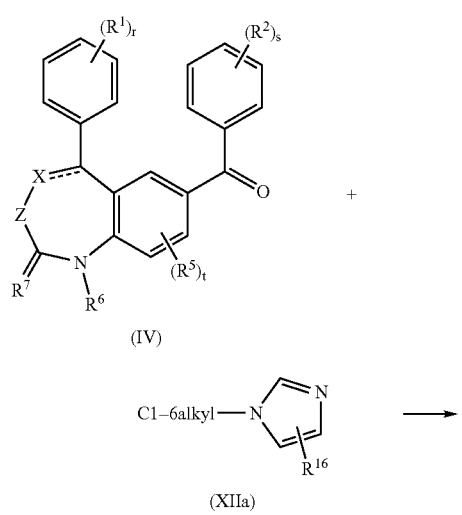

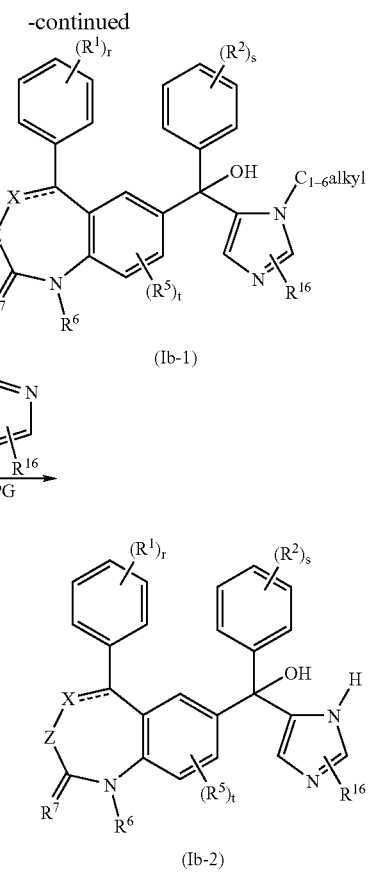

Also, the compounds of formula (I), wherein $R^4$ is a radical of formula (c-2), $R^3$ is hydroxy and $R^{17}$ is hydrogen, said compounds being referred to as compounds of formula (I-b-2) may be prepared by reacting an intermediate ketone of formula (IV) with a intermediate of formula (XIIb), wherein PG is a protective group such as, for example, a sulfonyl group, e.g. a dimethylamino sulfonyl group, which can be removed after the addition reaction. Said reaction is conducted analogously as for the preparation of compounds of formula (I-b-1), followed by removal of the protecting group PG, yielding compounds of formula (I-b-2).

Also with regard to process c), the compounds of formula (I) wherein $R^4$ represents a radical of formula (c-3) may be prepared by reacting the compound of formula (IV) with the triazole reagent, preferably in a reaction-inert solvent such as tetrahydrofuran, in the presence of a strong base such as butyl lithium at a temperature ranging from $-78°$ C. to room temperature. When the 3-mercapto derivative is methylated, this is conveniently effected with methyl iodide in the presence of a base such as sodium methylate. Removal of the 3-mercapto group is conveniently effected with sodium nitrite, for example in $THF/H_2O$ in the presence of nitric acid. Removal of the 3-methylmercapto group is conveniently effected with Raney Nickel in ethanol or acetone. Also the compounds of formula (1) wherein $R^4$ represents a radical of formula (c-4) may be prepared by reacting the compound of formula (IV) with the 3-bromopyridyl reagent, preferably in a reaction-inert solvent such as tetrahydrofuran, in the presence of a strong base such as butyl lithium at a temperature ranging from $-78°$ C. to room temperature.

Examples of the interconversion of one compound of formula (I) into a different compound of formula (I) include the following reactions:

a) compounds of formula (I-b) can be converted to compounds of formula (I-c), defined as a compound of formula (I) wherein $R^4$ is a radical of formula (c-2) and $R^3$ is hydrogen, by submitting the compounds of formula (I-b) to appropriate reducing conditions, such as, e.g. stirring in acetic acid in the presence of formamide, or treatment with sodium borohydride/trifluoroacetic acid.

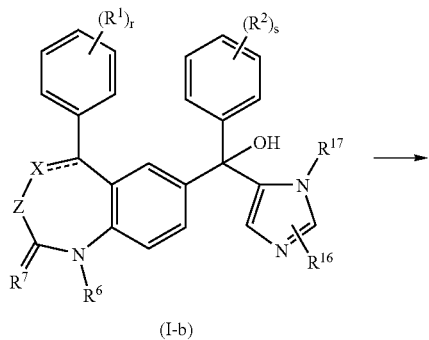

(I-b)

(I-c)

b) compounds of formula (I-b) can be converted to compounds of formula (I-f) wherein $R^3$ is halo, by reacting the compounds of formula (I-b) with a suitable halogenating agent, such as, e.g. thionyl chloride or phosphorus tribromide. Successively, the compounds of formula (I-f) can be treated with a reagent of formula H—$NR^{11}R^{12}$ in a reaction-inert solvent, thereby yielding compounds of formula (I-g).

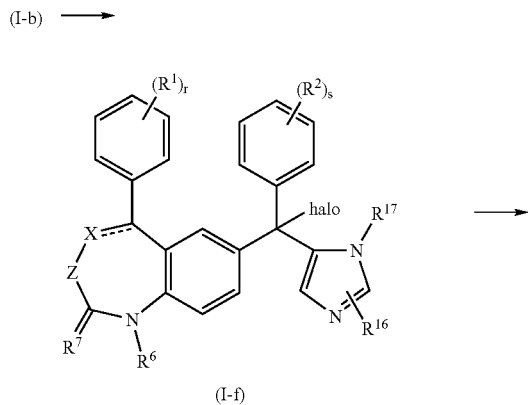

(I-b) →

(I-f)

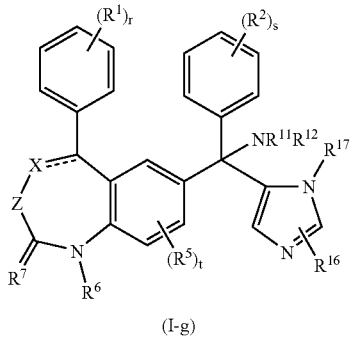

(I-g)

c) compounds of formula (I-b) can be converted into compounds of formula (I-g) for example by treatment with $SOCl_2$, and then $NH_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.;

d) compounds of formula (I-f) can be converted into compounds of formula (I-c) for example by treatment with $SnCl_2$ in the presence of concentrated HCl in acetic acid at reflux;

e) compounds of formula (I) in which $R^7$ is oxygen can be converted into corresponding compounds of formula (I) in which $R^7$ is sulphur with a reagent such as phosphorus pentasulfide or Lawesson's reagent in a suitable solvent such as, for example, pyridine;

f) compounds of formula (I) in which X is =N— can be converted into corresponding compounds of formula (I) in which X is —NH— by reaction with a reducing agent for example sodium borohydride;

g) compounds of formula (I) in which $R^6$ is H can be converted into corresponding compounds of formula (I) in which $R^6$ is $C_{1-6}$alkyl by reaction with an alkylating agent, for example methyl iodide in a reaction-inert solvent such as tetrahydofuran or dimethylformamide, in the presence of a base such as sodium hydride or under phase transfer catalysis conditions.

h) compounds of formula (I) in which $R^6$ is hydrogen and $R^7$ is sulphur can be converted into corresponding compounds of formula (I) in which $R^6$ and $R^7$ together form a trivalent radical of formula (x-4) by reaction with hydrazine and subsequent treatment of the resulting hydrazino product with a nitrite such as sodium nitrite, for example in accordance with the process described in the above WO 00/39082.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

The intermediates and starting materials used in the above-described processes may be prepared in conventional manner using procedures known in the art for example as described in the above-mentioned patent specifications WO 97/16443, WO 97/21701, WO 98/40383, WO 98/49157 and WO 00/39082. Thus for example, the starting materials used in processes b) and c) may be prepared by cyclisation procedures on appropriate starting materials, for example generally in accordance with the cyclisation procedures described above for process a) before the introduction of the imidazole moiety. For process c), it may be convenient to cyclise a compound of formula (XIII):

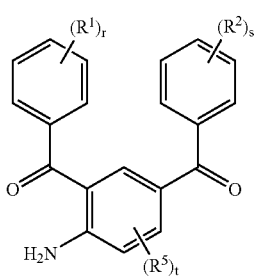

(XIII)

in which the keto group which is not involved in the cyclisation procedure may be protected for example with an ethylenedioxy protecting group. Thus, the above compound of formula (XIII) may be reduced for example with sodium borohydride and the protecting group removed under acidic conditions to form a compound of formula (XIV):

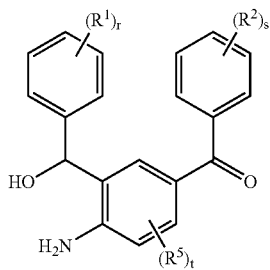

(XIV)

which is subsequently reacted with a compound of formula (V) or formula (VII) in analogous manner to process a) above to form starting materials in which X is —O— or —S— respectively. In the case where X is —NH— it may be convenient to react the compound of formula (XIII) with a compound of formula

H$_2$NZCOOC$_{1-6}$alkyl and subsequently cyclise the resulting product, and optionally reducing the C=N bond (where X is —N=) with an agent such as NaBH$_3$CN in acid media.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research,* 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neuro-fibromatosis, or tumors in which ras is activated due to mutation or overexpression of tyrosine kinase oncogenes, may be inhibited by the compounds of this invention.

The compound according to the invention can be used for other therapeutic purposes, for example:
 a) the sensitisation of tumors to radiotherapy by administering the compound according to the invention before, during or after irradiation of the tumor for treating cancer, for example as described in WO 00/01411;
 b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;
 c) inhibiting smooth muscle cell proliferation including vascular proliferative disorders, atherosclerosis and restenosis, for example as described in WO 98/55124;
 d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosis, Kawasaki's disease, multiple sclerosis, emphysema, cystic fibrosis and chronic bronchitis;
 e) treating endometriosis, uterine fibroids, dysfunctional uterine bleeding and endometrial hyperplasia;
 f) treating ocular vascularisation including vasculopathy affecting retinal and choroidal vessels;
 g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;
 h) inhibiting viral morphogenesis for example by inhibiting the prenylation or the post-prenylation reactions of a viral protein such as the large delta antigen of hepatitis D virus; and the treatment of HIV infections;
 i) treating polycystic kidney disease;
 j) suppressing induction of inducible nitric oxide including nitric oxide or cytokine mediated disorders, septic shock, inhibiting apoptosis and inhibiting nitric oxide cytotoxicity;
 k) treating malaria.

The compounds of present invention are particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other medicinal agents such as anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and antitumor podophyllotoxin derivatives for example etoposide or teniposide; and anti-estrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can administered to a patient as described above in conjunction with irradiation; such treatment is may be especially beneficial as farnesyl transferase inhibitors can act as radiosensitisers for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of
 administering a radiation-sensitizing effective amount of a farnesyl protein transferase inhibitor according to the invention before, during or after
 administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The following examples are provided for purposes of illustration.

Hereinafter "THF" means tetrahydrofuran, "DIPE" means diisopropyl ether, "DME" means 1,2-dimethoxyethane, "EtOAc" means ethyl acetate, "DCM" means dichloromethane and "BuLi" means n-butyl lithium. Where the absolute stereochemical configuration of a compound of formula (I) has not been identified, the stereochemically isomeric form which was first isolated is designated "A" and the second as "B", without reference to the actual stereochemical configuration.

A. Preparation of the Intermediates

EXAMPLE A1 a) Sodium tetrahydroborate (0.053 mol) was added to a mixture of (±)-[2-amino-5-[(4-chlorophenyl)hydroxy(1-methyl-1H-imidazol-5-yl)methyl]phenyl](3-chlorophenyl) methanone (prepared as described in WO 97/21701) (0.0442 mol) in methanol (250 ml). The mixture was stirred at room temperature for 1 hour, hydrolyzed and extracted with DCM. The organic layer was separated, dried ($MgSO_4$), filtered and the solvent was evaporated till dryness, yielding 23.3 g (>100%) of 4-amino-$\alpha^3$-(3-chlorophenyl)-$\alpha^1$-(4-chlorophenyl)-$\alpha^1$-(1-methyl-1H-imidazol-5-yl)-1,3-benzenedimethanol (intermediate 1).

b) Bromo-acetylbromide (0.0121 mol) was added to a mixture of intermediate (1) (0.011 mol) in $K_2CO_3$ 10% (130 ml) and DCM (200 ml). The mixture was stirred at room temperature for 2 hours. $K_2CO_3$ 10% was added. The mixture was extracted with DCM. The organic layer was separated, dried ($MgSO_4$), filtered and the solvent was evaporated till dryness, yielding 6.3 g (100%) of 2-bromo-N-[2-[(3-chlorophenyl)hydroxymethyl]-4-[(4-chlorophenyl)hydroxy(1-methyl-1H-imidazol-5-yl)methyl]phenyl]-acetamide (intermediate 2).

EXAMPLE A2

A mixture of intermediate (1) (0.011 mol) and mercapto-acetic acid (0.0094 mol) in HCl 6N (75 ml) was stirred and refluxed for 1 hour and then cooled. The solvent was evaporated till dryness, yielding 6.5 g (98%) of [[[2-amino-5-[(4-chlorophenyl)hydroxy(1-methyl-1H-imidazol-5-yl)methyl]phenyl](3-chlorophenyl)methyl]thio]-acetic acid hydrochloride salt (intermediate 3).

EXAMPLE A3 a) Bromo-acetyl bromide (0.0138 mol) was added slowly at 5° C. to a mixture of (±)-[2-amino-5-[(4-chlorophenyl)hydroxy(1-methyl-1H-imidazol-5-yl)methyl]phenyl](3-chlorophenyl)methanone (prepared as described in WO 97/21701) (0.0137 mol) in acetic acid (60 ml). The mixture was stirred for 15 min and poured out into EtOAc and NaOH 0.5N. The organic layer was separated, washed with water, dried ($MgSO_4$), filtered and the solvent was evaporated till dryness, yielding 7.3 g (93%) of 2-bromo-N-[2-(3-chlorobenzoyl)-4-[(4-chlorophenyl)hydroxy(1-methyl-1H-imidazol-5-yl)methyl]phenyl]-acetamide (intermediate 4).

b) A mixture of intermediate (4) (0.0161 mol) and $NaN_3$ (0.0161 mol) in methanol (25 ml) was stirred and refluxed overnight. The product was used without further purification, yielding 2-azido-N-[2-(3-chlorobenzoyl)-4-[(4-chlorophenyl)hydroxy(1-methyl-1H-imidazol-5-yl)methyl]phenyl]-acetamide (intermediate 5).

EXAMPLE A4 a) Ethyl ester glycine, hydrochloride (0.081 mol) was added to a mixture of 1-amino-2,4-phenylene(3-chlorophenyl)(4-chlorophenyl)dimethanone (prepared as described in WO 97/16443) (0.054 mol) and molecular sieves (q.s.) in pyridine (200 ml). The mixture was stirred and refluxed for 48 hours. The solvent was evaporated till dryness. The residue was taken up in water and DCM and the mixture was decanted. The organic layer was washed with HCl 3N and with $K_2CO_3$ 10%, dried, filtered and the solvent was evaporated. Part (1.3 g) of this fraction (11.8 g) was crystallized from 2-propanone and methanol. The precipitate was filtered off and dried, yielding 1.15 g (88%) of 7-(4-chlorobenzoyl)-5-(3-chlorophenyl)-1,3-dihydro-2H-1,4-benzodiazepin-2-one (intermediate 6), mp. 265° C.

b) NaH 80% in oil (0.0366 mol) was added at 10° C. under $N_2$ flow to a mixture of intermediate (6) (0.0244 mol)

in N,N-dimethylformamide (100 ml). The mixture was brought to room temperature and then stirred for 30 min. and iodomethane (0.0293 mol) was added. The mixture was stirred for 3 hours, hydrolyzed, filtered, washed with water and taken up in DCM. The organic layer was separated, dried ($MgSO_4$), filtered and the solvent was evaporated till dryness. The residue (9.1 g) was purified by column chromatography over silica gel (eluent: $CH_2Cl_2/CH_3OH$ 98/2; 15–40 μm). The pure fractions were collected and the solvent was evaporated. The residue was crystallized from 2-propanone. The precipitate was filtered off and dried, yielding 4.5 g (43%) of 7-(4-chlorobenzoyl)-5-(3-chlorophenyl)-1,3-dihydro-1-methyl-2H-1,4-benzodiazepin-2-one (intermediate 7), mp. 176° C.

c) $NaBH_3CN$ (0.0472 mol) was added at 5° C. to a mixture of intermediate (7) (0.0236 mol) in acetic acid (50 ml) and methanol (300 ml). The mixture was stirred at 5° C. for 30 min and then stirred at room temperature for 2 hours. Ice water and then $NH_4OH$ 35% (60 ml) were added. The mixture was stirred for 2 hours. The precipitate was filtered off, washed with water and taken up in DCM. The organic layer was separated, dried ($MgSO_4$), filtered and the solvent was evaporated, yielding 8.25 g (85%) of 7-(4-chlorobenzoyl)-5-(3-chlorophenyl)-1,3,4,5-tetrahydro-1-methyl-2H-1,4-benzodiazepin-2-one (intermediate 8), mp. 177° C.

EXAMPLE A5 a) A mixture of [2-amino-5-[2-(4-chlorophenyl)-1,3-dioxolan-2-yl]phenyl](3-chlorophenyl)methanone (prepared as described in WO 98/49157) (0.088 mol) in methanol (300 ml) and THF (100 ml) was cooled on an ice bath. sodium tetrahydroborate (0.088 mol) was added portionwise. The mixture was stirred at a low temperature for 30 min, then hydrolized and extracted with DCM. The organic layer was separated, dried ($MgSO_4$), filtered and the solvent was evaporated till dryness. The product was used without further purification, yielding 36.6 g (100%) of 2-amino-α-(3-chlorophenyl)-5-[2-(4-chlorophenyl)-1,3-dioxolan-2-yl]-benzenemethanol (intermediate 9).

b) $K_2CO_3$ 10% (250 ml) was added to a mixture of intermediate (9) (0.072 mol) in DCM (250 ml). Then bromoacetyl bromide (0.072 mol) was added dropwise at room temperature. The mixture was stirred at room temperature overnight. The organic layer was separated, dried ($MgSO_4$), filtered and the solvent was evaporated till dryness. The product was used without further purification, yielding (quant.) of 2-bromo-N-[4-[2-(4-chlorophenyl)-1,3-dioxolan-2-yl]-2-[(3-chlorophenyl)hydroxymethyl]phenyl]-acetamide (intermediate 10).

c) A mixture of intermediate (10) (0.072 mol) in DME (300 ml) was cooled on an ice bath. 2-methyl-2-propanol, potassium salt (0.144 mol) was added portionwise. The mixture was stirred at a low temperature for 30 min, at room temperature for 30 min, hydrolyzed and acidified with HCl. The precipitate was filtered off, rinced and dried, yielding 17 g (51.8%) of 5-(3-chlorophenyl)-7-[2-(4-chlorophenyl)-1,3-dioxolan-2-yl]-1,5-dihydro-4,1-benzoxazepin-2(3H)-one (intermediate 11), mp. 205° C.

d) Tetraphosphorus decasulfide (0.0305 mol) was added to a solution of intermediate (11) (0.0254 mol) in THF (300 ml). The mixture was stirred at 40° C. for 1 hour and then cooled. DCM was added. The precipitate was filtered off. The filtrate was washed with water, dried ($MgSO_4$), filtered and the solvent was evaporated till dryness. The residue (16 g) was purified by column chromatography over silica gel (eluent: $CH_2Cl_2$/EtOAc 99.5/0.5; 20–45 μm). The pure fractions were collected and the solvent was evaporated. The residue was crystallized from 2-propanone and DIPE. The precipitate was filtered off and dried, yielding 1.5 g (13.8%) of (4-chlorophenyl)[5-(3-chlorophenyl)-1,2,3,5-tetrahydro-2-thioxo-4,1-benzoxazepin-7-yl]-methanone(intermediate 12), mp. 158° C.

EXAMPLE A6 a) A mixture of intermediate (6) (0.01 mol) and tetraphosphorus decasulfide (0.012 mol) in THF (100 ml) was stirred at 60° C. for 6 hours, poured out into ice water and stirred for 1 hour. DCM was added. The mixture was stirred for 30 min, filtered over celite and washed several times with DCM. The organic layer was separated, dried ($MgSO_4$), filtered and the solvent was evaporated till dryness. The residue (2.85 g) was purified by column chromatography over silica gel (eluent: $CH_2Cl_2$ 100%; 35–70 μm). The pure fractions were collected and the solvent was evaporated. The residue (1.3 g, 30.5%) was crystallized from acetonitrile. The precipitate was filtered off and dried, yielding 1.1 g (26%) of (4-chlorophenyl)[5-(3-chlorophenyl)-2,3-dihydro-2-thioxo-1H-1,4-benzodiazepin-7-yl]-methanone (intermediate 13), mp. 125° C.

b) Hydrazine (1.5 ml) was added to a mixture of intermediate (13) (0.00353 mol) in THF (20 ml). The mixture was stirred at room temperature for 15 min. $K_2CO_3$ 10% was added and the mixture was extracted with DCM. The organic layer was separated, dried ($MgSO_4$), filtered and the solvent was evaporated till dryness, yielding 1.5 g (100%) of (4-chlorophenyl)[5-(3-chlorophenyl)-2-hydrazino-3H-1,4-benzodiazepin-7-yl]-methanone (intermediate 14).

c) HCl 0.5N (30 ml) was cooled. Intermediate (14) (0.00353 mol) was added. The mixture was cooled while stirring vigorously. A solution of sodium nitrite (0.0037 mol) in water (8 ml) was added dropwise. The mixture was stirred at 5° C. for 45 min, basified with $K_2CO_3$ 10% and extracted with DCM. The organic layer was separated, dried ($MgSO_4$), filtered and the solvent was evaporated till dryness. The residue (1.6 g) was purified by column chromatography over silica gel (eluent: $CH_2Cl_2$ 100%; 35–70 μm). The pure fractions were collected and the solvent was evaporated. The residue was crystallized from acetonitrile. The precipitate was filtered off, washed with diethyl ether and dried, yielding 1 g (65%) of (4-chlorophenyl)[6-(3-chlorophenyl)-4H-tetrazolo[1,5-a][1,4]benzodiazepin-8-yl]-methanone (intermediate 15), mp. 220° C.

EXAMPLE A7 a) $TiCl_3$ 15% in water (35 ml) was added slowly to a mixture of (±)-3-(3-chlorophenyl)-α-(4-chlorophenyl)-α-(1-methyl-1H-imidazol-5-yl)-2,1-benzisoxazole-5-methanol (prepared as described in WO 97/21701) (0.0111 mol) in THF (50 ml). The mixture was stirred at room temperature for 24 hours, basified with NaOH 3N, extracted with DCM, filtered over celite and pasted up with DCM. The organic layer was separated, dried ($MgSO_4$), filtered and the solvent was evaporated till dryness. The residue (4.4 g) was purified by column chromatography over silica gel (eluent: $CH_2Cl_2$/$CH_3OH$/$NH_4OH$ 96/4/0.1; 20–45 μm). Two pure fractions were collected and their solvents were evaporated, yielding 1.6 g F1 (34%) and 1 g of 2-amino-α-(3-chlorophenyl)-5-[(4-chlorophenyl)(1-methyl-1H-imidazol-5-yl)methyl]-benzene methanol (21%). F1 was crystallized from acetonitrile and DIPE. The precipitate was filtered off, washed with diethyl ether and dried, yielding 0.8 g (16.5%) of [2-amino- 5-[(4-chlorophenyl)(1-methyl-1H-imidazol-5-yl)methyl] phenyl](3-chlorophenyl)-methanone (intermediate 16), mp. 179° C.

b) A mixture of intermediate (16) (0.0848 mol) in methanol (400 ml) was cooled to 10° C. sodium tetrahydroborate (0.102 mol) was added portionwise. The mixture was stirred at room temperature for 2 hours, poured out into ice water and extracted with DCM. The organic layer was separated, washed with water, dried (MgSO$_4$), filtered and the solvent was evaporated. The residue was purified by column chromatography over silica gel (eluent: CH$_2$Cl$_2$/CH$_3$OH/ NH$_4$OH 95/5/0.1; 20–45 μm). The pure fractions were collected and the solvent was evaporated, yielding 12.3 g (33%) of 2-amino-α-(3-chlorophenyl)-5-[(4-chlorophenyl) (1-methyl-1H-imidazol-5-yl)methyl]-benzenemethanol (intermediate 17).

c) A mixture of intermediate (17) (0.0269 mol) and mercapto-acetic acid (0.0269 mol) in HCl 6N (150 ml) was stirred and refluxed for 2 hours and brought to room temperature. The solvent was evaporated till dryness, yielding 15 g (96%) of [[[2-amino-5-[(4-chlorophenyl)(1-methyl-1H-imidazol-5-yl)methyl]phenyl](3-chlorophenyl)methyl] thio]-acetic acid hydrochloride salt (intermediate 18).

EXAMPLE A8 a) A mixture of intermediate (9) (0.088 mol) and mercapto-acetic acid (0.0836 mol) in HCl 6N (500 ml) was stirred and refluxed for 1 hour, then cooled and poured out into ice water. The precipitate was filtered off, washed with water and taken up in DCM. The organic solution was dried (MgSO$_4$), filtered and the solvent was evaporated till dryness. The product was used without further purification, yielding 35.5 g (90.5%) of [[[2-amino-5-(4-chlorobenzoyl) phenyl](3-chlorophenyl)methyl]thio]-acetic acid (intermediate 19).

b) A mixture of intermediate (19) (0.079 mol) and MgSO4 (35.5 g) in toluene (500 ml) was stirred and refluxed overnight in a Dean-Stark apparatus and then cooled. The precipitate was filtered off and the filtrate was evaporated till dryness. The residue (35 g) was purified by column chromatography over silica gel (eluent: CH$_2$Cl$_2$/EtOAc 85/15; 20–45 μm). The pure fractions were collected and the solvent was evaporated. The residue was crystallized from acetonitrile and DIPE. The precipitate was filtered off and dried, yielding 1.5 g (4.4%) of 7-(4-chlorobenzoyl)-5-(3-chlorophenyl)-1,5-dihydro-4,1-benzothiazepin-2(3H)-one (intermediate 20), mp. 222° C.

c) Tetraphosphorus decasulfide (0.0075 mol) was added to a solution of intermediate (20) (0.0063 mol) in THF (50 ml). The mixture was stirred at 40° C. for 1 hour and then brought to room temperature. DCM was added. The precipitate was filtered off. The filtrate was washed with water, dried (MgSO$_4$), filtered and the solvent was evaporated till dryness. The residue (5 g) was purified by column chromatography over silica gel (eluent: CH$_2$Cl$_2$ 100%; 15–40 μm). The pure fractions were collected and the solvent was evaporated. The residue was crystallized from acetonitrile and DIPE. The precipitate was filtered off and dried, yielding 1.7 g (60.7%) of (4-chlorophenyl)[5-(3-chlorophenyl)-1,2,3,5-tetrahydro-2-thioxo-4,1-benzothiazepin-7-yl]-methanone (intermediate 21), mp. 224° C.

EXAMPLE A9

3-mercapto-propanoic acid (0.00433 mol) was added slowly to a mixture of intermediate (17) (0.00456 mol) in dioxane (20 ml) and D (20 ml). The mixture was stirred at 80° C. for 5 hours. The solvent was evaporated till dryness. The product was used without further purification, yielding 3-[[[2-amino-5-[(4-chlorophenyl)(1-methyl-1H-imidazol-5-yl)methyl]phenyl](3-chlorophenyl)methyl]thio]-propanoic acid (intermediate 22).

EXAMPLE A10 a) 2-(4-chlorophenyl)-2-(4-nitrophenyl)-1,3-dioxolane (prepared as described in WO 97/21701) (0.0373 mol) was added to a vigorously stirring mixture of benzene acetonitrile (0.041 mol) and NaOH (0.186 mol) in methanol (37.3 ml) (an exothermic effect was observed and the temperature rose to 45° C.) and the mixture was stirred vigorously for 20 h. The mixture was diluted with water and filtered off. The precipitate was washed with water and a few methanol and dried. A part (3.5 g) of the residue (10.59 g, 75%) was purified by column chromatography over silica gel (eluent: DCM). The pure fractions were collected and evaporated. The residue (2.94 g) was crystallized from DIPE, yielding 2.3 g of 5-[2-(4-chlorophenyl)-1,3-dioxolan-2-yl]-3-phenyl-2,1-benzisoxazole, mp. 143.4° C. (intermediate 23).

b) Intermediate (23) (0.088 mol) in THF (500 ml) was hydrogenated with Pd/C 10% (3.3 g) as a catalyst at room temperature for 3 h under a 1.8/2 bar pressure in a Parr apparatus. After uptake of H$_2$ (1 eq), the catalyst was filtered off and the filtrate was evaporated in vacuo. The residue (35.3 g) was recrystallized from DCM/DIPE, yielding 20 g (60%) of [2-amino-5-[2-(4-chlorophenyl)-1,3-dioxolan-2-yl]phenyl]phenylmethanone, (intermediate 24).

c) A mixture of intermediate (24) (0.105 mol) in bromoacetyl bromide (27.6 ml) and benzene (360 ml) was stirred and refluxed for 4 h. The mixture was cooled and EtOAc was added. The organic layer was washed with NaOH 1N and water, dried (MgSO$_4$), filtered off and evaporated. The product was used without further purification, yielding 2-bromo-N-[2-benzoyl-4-[2-(4-chlorophenyl)-1,3-dioxolan-2-yl]phenyl]acetamide (intermediate 25).

d) A mixture of intermediate (25) (0.105 mol) and sodium azide (6.84 g) in methanol (160 ml) was stirred and refluxed for 6 h. The mixture was cooled, poured into ice water and extracted with DCM. The organic layer was dried (MgSO$_4$), filtered off and evaporated till dryness. The product was used without further purification, yielding 2-azido-N-[2-benzoyl-4-[2-(4-chlorophenyl)-1,3-dioxolan-2-yl]phenyl]acetamide (intermediate 26).

e) Intermediate (26) (0.1052 mol) in THF (220 ml) was hydrogenated with Pd/C (0.6 g) as a catalyst at room temperature for 8 h under a 2 bar pressure in a Parr apparatus. After uptake of H$_2$, the catalyst was filtered over celite and the filtrate was evaporated till dryness. The residue (47.9 g) was purified by column chromatography over silica gel (eluent: CH$_2$Cl$_2$/CH$_3$OH/NH$_4$OH 98/2/0.1) (35–70 μm). The pure fractions were collected and evaporated and the residue was crystallized from 2-propanone/ DIPE giving 14.86 g (31%). A sample (1.35 g) was taken up in hot ethanol and filtered off, yielding 0.93 g (70%) of 7-(4-chlorobenzoyl)-1,3-dihydro-5-phenyl-2H-1,4-benzodiazepin-2-one (intermediate 27), mp. 230° C.

f) Sodium tetrahydroborate (2.68 g) was added portionwise at 5° C. to a solution of intermediate (27) (0.0354 mol) in methanol (150 ml). The solution was poured into ice water and extracted with DCM. The organic layer was dried (MgSO$_4$), filtered off and evaporated. The residue (12.27 g) was purified by column chromatography over silica gel (eluent: CH$_2$Cl$_2$/CH$_3$OH/NH$_4$OH 97/3/0.1). The pure fractions were collected and evaporated. The residue was crystallized from methanol, yielding 10.4 g (78%) of (±)-7-[(4-chlorophenyl)hydroxymethyl]-1,3-dihydro-5-phenyl-2H-1,4-benzodiazepin-2-one (intermediate 28).

g) A mixture of intermediate (28) (0.0125 mol) in thionyl chloride (5 ml) and DCM (100 ml) was stirred at room temperature overnight. The mixture was evaporated till dryness. The product was used without further purification, yielding 4.93 g (100%) of (±)-7-[chloro(4-chlorophenyl)methyl]-1,3-dihydro-5-phenyl-2H-1,4-benzodiazepin-2-one (intermediate 29).

EXAMPLE A11 a) Hydrazine (3.25 ml) was added at room temperature to a mixture of intermediate (21) (0.01125 mol) in THF (100 ml). The mixture was stirred at room temperature for 15 min, poured out into water and extracted with DCM. The organic layer was separated, dried, filtered and the solvent was evaporated, yielding (quant.) of (4-chlorophenyl)[5-(3-chlorophenyl)-2-hydrazino-3,5-dihydro-4,1-benzothiazepin-7-yl]-methanone (intermediate 30).

b) Intermediate (30) (0.01125 mol) was cooled on an ice bath. Hydrochloric acid (90 ml) was added. Then a solution of sodium nitrite (0.013 mol) in water (18 ml) was added quickly dropwise. The mixture was stirred at 5° C. for 30 min and at room temperature for 2 hours. Water was added. The mixture was basified with $K_2CO_3$ 10% and extracted with DCM. The organic layer was separated, dried ($MgSO_4$), filtered and the solvent was evaporated till dryness. The residue (6 g) was purified by column chromatography over silica gel (eluent: $CH_2Cl_2/CH_3OH$ 90/10; 15–40 μm). The pure fractions were collected and the solvent was evaporated. The residue was crystallized from DCM/DIPE. The precipitate was filtered off and dried, yielding 1 g (19.6%) of (4-chlorophenyl)[6-(3-chlorophenyl)-4H,6H-tetrazolo[1,5-a][4,1]benzothiazepin-8-yl]-methanone (intermediate 31), mp. 212° C.

B. Preparation of the Compounds

EXAMPLE B1

2-methyl, 2-propanol, potassium salt (0.044 mol) was added to a mixture of intermediate (2) (0.011 mol) in 2-propanol (160 ml). The mixture was stirred for 48 hours, hydrolized and extracted with DCM and methanol. The organic layer was separated, dried ($MgSO_4$), filtered and the solvent was evaporated till dryness. The residue (4.1 g) was purified by column chromatography over silica gel (eluent: toluene/2-propanol/$NH_4OH$ 90/10/1 and 85/15/1; 15–40 μm). The pure fractions were collected and the solvent was evaporated. The residue was crystallized from 2-propanone and diethyl ether. The precipitate was filtered off and dried, yielding 0.58 g (11%) of 5-(3-chlorophenyl)-7-[(4-chlorophenyl)hydroxy(1-methyl-1H-imidazol-5-yl)methyl]-1,5-dihydro-4,1-benzoxazepin-2(3H)-one, mp. 260° C.

EXAMPLE B2

A mixture of intermediate (3) (0.0103 mol) and $MgSO_4$ (6.2 g) in toluene (155 ml) was stirred and refluxed for 5 hours, then filtered and washed with $CH_2Cl_2/CH_3OH$ 1/2. The organic layer was separated, washed with $K_2CO_3$ 10%, dried ($MgSO_4$), filtered and the solvent was evaporated till dryness. The residue (3.35 g) was purified by column chromatography over silica gel (eluent: $CH_2Cl_2/CH_3OH/NH_4OH$ 96/4/0.1; 15–40 μm). The pure fractions were collected and the solvent was evaporated. The residue was crystallized from 2-propanone and diethyl ether. The precipitate was filtered off and dried, yielding 1.6 g (30%) of 5-(3-chlorophenyl)-7-[(4-chlorophenyl)hydroxy(1-methyl-1H-imidazol-5-yl)methyl]-1,5-dihydro-4,1-benzothiazepin-2(3H)-one, mp. 210° C.

EXAMPLE B3

NaH 80% in oil (0.0069 mol) was added portionwise to a mixture of 5-(3-chlorophenyl)-7-[(4-chlorophenyl)hydroxy(1-methyl-1H-imidazol-5-yl)methyl]-1,5-dihydro-4,1-benzoxazepin-2(3H)-one (see Example B1) (0.0069 mol) in N,N-dimethylformamide (35 ml). The mixture was stirred at room temperature for 30 min. Iodomethane (0.0069 mol) was added. The mixture was stirred at room temperature for 30 min, hydrolized and extracted with DCM. The organic layer was separated, dried ($MgSO_4$), filtered and the solvent was evaporated till dryness. The residue (4.1 g) was purified by column chromatography over silica gel (eluent: $CH_2Cl_2/CH_3OH/NH_4OH$ 97/3/0.1; 15–40 μm). The pure fractions were collected and the solvent was evaporated. The residue was crystallized from 2-propanone and diethyl ether. The precipitate was filtered off and dried, yielding 0.47 g (13%) of 5-(3-chlorophenyl)-7-[(4-chlorophenyl)hydroxy(1-methyl-1H-imidazol-5-yl)methyl]-1,5-dihydro-1-methyl-4,1-benzoxazepin-2(3H)-one, mp. 160° C.

EXAMPLE B4

A mixture of intermediate (5) (0.0161 mol) in methanol (35 ml) was hydrogenated at room temperature under a 2 bar pressure for 15 min with Pd/C 10% (1 g) as a catalyst. After uptake of $H_2$ (1 equiv), the catalyst was filtered off and the filtrate was evaporated. DCM was added and the mixture was filtered through celite. The organic layer was separated, dried ($MgSO_4$), filtered and the solvent was evaporated till dryness. The residue was purified over silica gel on a glass filter (eluent: $CH_2Cl_2/CH_3OH$ 98/2, 95/5 and 90/10). The pure fractions were collected and the solvent was evaporated. The residue (3.4 g) was purified by column chromatography over silica gel (eluent: toluene/2-propanol/$NH_4OH$ 85/15/1; 15–40 μm). The pure fractions were collected and the solvent was evaporated. The residue was crystallized from 2-propanone. The precipitate was filtered off, washed with diethyl ether and dried, yielding 1 g (12%) of 5-(3-chlorophenyl)-7-[(4-chlorophenyl)hydroxy(1-methyl-1H-imidazol-5-yl)methyl]-1,3-dihydro-2H-1,4-benzodiazepin-2-one, mp. 200° C.

EXAMPLE B5

BuLi 1.6M in hexane (27.4 ml) was added dropwise at –70° C. under $N_2$ flow to a mixture of 1-methyl-1H-imidazole (0.0439 mol) in THF (140 ml). The mixture was stirred for 30 min. ClSiEt$_3$ (0.0439 mol) was added. The mixture was brought slowly to room temperature and cooled again to –70° C. BuLi 1.6M in hexane (27.4 ml) was added dropwise. The mixture was stirred for 1 hour, brought quickly to –15° C. and cooled to –70° C. A solution of intermediate (8) (0.02 mol) in THF (90 ml) was added dropwise. The mixture was stirred at –50° C. for 30 min, then hydrolyzed and extracted with EtOAc. The organic layer was separated, dried ($MgSO_4$), filtered and the solvent was evaporated till dryness. The residue (17.5 g) was purified by column chromatography over silica gel (eluent: $CH_2Cl_2/CH_3OH/NH_4OH$ 94/6/0.1 and 93/7/0.1; 20–45 μm). The pure fractions were collected and the solvent was evaporated. The residue was crystallized from CH$_3$CN, EtOAc and 2-propanone. The precipitate was filtered off and dried, yielding 0.8 g (8.5%) of 5-(3-chlorophenyl)-7-[(4-chlorophenyl)hydroxy(1-methyl-1H-imidazol-5-yl)methyl]-1,3,4,5-tetrahydro-1-methyl-2H-1,4-benzodiazepin-2-one, mp. 208° C.

EXAMPLE B6

NaH 60% (0.00917 mol) was added portionwise at 5° C. under N$_2$ flow to a mixture of 5-(3-chlorophenyl)-7-[(4-chlorophenyl)hydroxy(1-methyl-1H-imidazol-5-yl)methyl]-1,5-dihydro-4,1-benzothiazepin-2(3H)-one (see Example B2) (0.00705 mol) in THF (50 ml). The mixture was stirred for 30 min. Iodomethane (0.00846 mol) was added dropwise. The mixture was stirred at 5° C. for 1 hour, at room temperature for 2 hours and hydrolyzed cold. EtOAc was added. The mixture was filtered over celite, washed with EtOAc and the filtrate was extracted with EtOAc. The organic layer was separated, washed with water, dried (MgSO$_4$), filtered and the solvent was evaporated. The residue was crystallized from 2-propanone and diethyl ether. The precipitate was filtered off and dried in vacuo, yielding 2.5 g (67%) of 5-(3-chlorophenyl)-7-[(4-chlorophenyl)hydroxy(1-methyl-1H-imidazol-5-yl)methyl]-1,5-dihydro-1-methyl-4,1-benzothiazepin-2(3H)-one, mp. 186° C.

EXAMPLE B7

BuLi 1.6M (10.2 ml) was added dropwise at –70° C. under N$_2$ flow to a mixture of 1-methyl-1H-imidazole (0.0164 mol) in THF (25 ml). The mixture was stirred at –70° C. for 30 min. ClSiEt$_3$ (0.0164 mol) was added. The mixture was brought slowly to 10° C. and cooled again to –70° C. BuLi 1.6M (10.2 ml) was added dropwise. The mixture was stirred at –70° C. for 1 hour, brought to –30° C. and cooled again to –70° C. A mixture of intermediate (12) (0.00747 mol) in THF (35 ml) was added dropwise. The mixture was brought to room temperature, hydrolyzed and extracted with EtOAc. The organic layer was separated, dried (MgSO$_4$), filtered and the solvent was evaporated till dryness. The residue (8 g) was purified by column chromatography over silica gel (eluent: CH$_2$Cl$_2$/CH$_3$OH/NH$_4$OH 95/5/0.1; 15–40 μm). The desired fractions were collected and the solvent was evaporated. The residue was crystallized from 2-propanone, acetonitrile and DIPE. The precipitate was filtered off and dried, yielding 1 g (26.3%) of 5-(3-chlorophenyl)-7-[(4-chlorophenyl)hydroxy(1-methyl-1H-imidazol-5-yl)methyl]-1,5-dihydro-4,1-benzoxazepine-2(3H)-thione, mp. >300° C.

EXAMPLE B8

BuLi 1.6M in hexane (7.5 ml) was added dropwise at –70° C. to a mixture of 1-methyl-1-H-imidazole (0.012 mol) in THF (20 ml). The mixture was stirred for 30 min. ClSiEt$_3$ (0.012 mol) was added. The mixture was brought slowly to room temperature and cooled again to –70° C. BuLi 1.6M in hexane (7.5 ml) was added dropwise. The mixture was stirred for 1 hour, brought quickly to –15° C., cooled again to –70° C. and poured out into to a solution of intermediate (7) (0.0118 mol) in THF (50 ml). The mixture was stirred for 30 min, then hydrolyzed and extracted with DCM. The organic layer was separated, dried (MgSO$_4$), filtered and the solvent was evaporated till dryness. The residue (8 g) was purified by column chromatography over silica gel (eluent: CH$_2$Cl$_2$/CH$_3$OH/NH$_4$OH 97/3/0.1; 15–40 μm). Two pure fractions were collected and their solvents were evaporated, yielding 2.7 g F1(54%, starting material) and 2.3 g F2 (38.5%). F2 was crystallized from acetonitrile. The precipitate was filtered off and dried, yielding 1.7 g (28.5%) of 5-(3-chlorophenyl)-7-[(4-chlorophenyl)hydroxy(1-methyl-1H-imidazol-5-yl)methyl]-1,3-dihydro-1-methyl-2H-1,4-benzodiazepin-2-one, mp. 226° C.

EXAMPLE B9

BuLi 1.6M in hexane (3.33 ml) was added dropwise at –70° C. to a mixture of 1-methyl-1-H-imidazole (0.0053 mol) in THF (10 ml). The mixture was stirred for 30 min. ClSiEt$_3$ (0.0053 mol) was added. The mixture was brought slowly to room temperature and cooled again to –70° C. C (3.33 ml) was added dropwise. The mixture was stirred for 1 hour, brought quickly to –15° C. and cooled again to –70° C. A mixture of intermediate (15) (0.0052 mol) in THF (25 ml) was added dropwise at –70° C. The mixture was stirred for 30 min, brought to –40, hydrolyzed and extracted with DCM. The organic layer was separated, dried (MgSO$_4$), filtered and the solvent was evaporated till dryness. The residue (3.4 g) was purified by column chromatography over silica gel (eluent: CH$_2$Cl$_2$/CH$_3$OH/NH$_4$OH 97.5/2.5/0.1; 15–40 μm). Two pure fractions were collected and their solvents were evaporated, yielding 1.95 g F1 (86%) and 0.19 g F2 (7.1%). F1 was crystallized from acetonitrile. The precipitate was filtered off and dried, yielding 1.7 g of starting material (75%). F2 was crystallized from 2-propanone, acetonitrile and diethyl ether. The precipitate was filtered off and dried, yielding 0.16 g (6%) of 6-(3-chlorophenyl)-α-(4-chlorophenyl)-α-(1-methyl-1H-imidazol-5-yl)-4H-tetrazolo[1,5-a][1,4]benzodiazepine-8-methanol, mp. 240° C.

EXAMPLE B10 a) 5-(3-chlorophenyl)-7-[(4-chlorophenyl)hydroxy(1-methyl-1H-imidazol-5-yl)methyl]-1,3-dihydro-1-methyl-2H-1,4-benzodiazepin-2-one (see Example B8) (0.0075 mol) was added portionwise at 5° C. to thionyl chloride (40 ml). The mixture was stirred at 5° C. for 6 hours. The solvent was evaporated till dryness. The product was used without further purification, yielding 7-[chloro(4-chlorophenyl)(1-methyl-1H-imidazol-5-yl)methyl]-5-(3-chlorophenyl)-1,3dihydro-1-methyl-2H-1,4-benzodiazepin-2-one.

b) NH$_3$/2-propanol (40 ml) was added dropwise at 5° C. to a mixture of 7-[chloro(4-chlorophenyl)(1-methyl-1H-imidazol-5-yl)methyl]-5-(3-chlorophenyl)-1,3-dihydro-1-methyl-2H-1,4-benzodiazepin-2-one (described in Example B10a) (0.0075 mol) in THF (40 ml). The mixture was stirred at 5° C. for 30 min, hydrolyzed and extracted with DCM. The organic layer was separated, dried (MgSO$_4$), filtered and the solvent was evaporated till dryness. The residue (4 g) was purified by column chromatography over silica gel (eluent: CH$_2$Cl$_2$/CH$_3$OH/NH$_4$OH 97.5/2.5/0.1 and 96/4/0.1; 15–40 μm). The pure fractions were collected and the solvent was evaporated. The residue was crystallized from acetonitrile and diethyl ether. The precipitate was filtered off and dried, yielding 1.8 g (48%) of 2H-1,4-benzodiazepin-2-one, 7-[amino(4-chlorophenyl)(1-methyl-1H-imidazol-5-yl)methyl]-5-(3-chlorophenyl)-1,3-dihydro-1-methyl-2H-1,4-benzodiazepin-2-one, mp. 213° C.

EXAMPLE B11 a) 5-(3-chlorophenyl)-7-[(4-chlorophenyl)hydroxy(1-methyl-1H-imidazol-5-yl)methyl]-1,5-dihydro-1-methyl-4,1-benzothiazepin-2(3H)-one (see Example B6) (0.00248 mol) was added at 5° C. under N$_2$ flow to thionyl chloride (15 ml). The mixture was stirred at 5° C. for 1 hour and at room temperature for 2 hours. The solvent was evaporated till dryness. The residue was taken up in DCM. The solvent was evaporated till dryness. The product was used without further purification, yielding 1.5 g (quant.) 7-[chloro(4-chlorophenyl)(1-methyl-1H-imidazol-5-yl)methyl]-5-(3-chlorophenyl)-1,5-dihydro-1-methyl-4,1-benzothiazepin-2(3H)-one.

b) NH$_3$/2-propanol (10 ml) was added dropwise at 5° C. under N$_2$ flow to a mixture of 7-[chloro(4-chlorophenyl)(1-methyl-1H-imidazol-5-yl)methyl]-5-(3-chlorophenyl)-1,5-dihydro-1-methyl-4,1-benzothiazepin-2(3H)-one (described in Example B11a) (0.00247 mol) in THF (15 ml). The mixture was stirred at 5° C. for 1 hour and at room temperature for 2 hours, then poured out into ice water and extracted with CH$_2$Cl$_2$. The organic layer was separated, washed with water, dried (MgSO$_4$), filtered and the solvent was evaporated. The residue (1.2 g) was purified by column chromatography over silica gel (eluent: CH$_2$Cl$_2$/CH$_3$OH/NH$_4$OH 97/3/0.5; 15–40 μm). The pure fractions were collected and the solvent was evaporated. The residue (0.35 g, 27%). was crystallized from acetonitrile and diethyl ether. The precipitate was filtered off and dried in vacuo, yielding 0.28 g (22%) of 7-[amino(4-chlorophenyl)(1-methyl-1H-imidazol-5-yl)methyl]-5-(3-chlorophenyl)-1,5-dihydro-1-methyl-4,1-benzothiazepin-2(3H)-one, mp. 218° C.

EXAMPLE B12 a) A mixture of 6-(3-chlorophenyl)-α-(4-chlorophenyl)-α-(1-methyl-1H-imidazol-5-yl)-4H-tetrazolo[1,5-a][1,4]benzodiazepine-8-methanol (see Example B9) (0.0015 mol) in thionyl chloride (10 ml) was stirred at 5° C. for 5 hours. The solvent was evaporated till dryness. The product was used without further purification, yielding 8-[chloro(4-chlorophenyl)(1-methyl-1H-imidazol-5-yl)methyl]-6-(3-chlorophenyl)-4H-tetrazolo[1,5-a][1,4]benzodiazepine.

b) 2-propanol/NH$_3$ (10 ml) was added dropwise at 5° C. to a mixture of 8-[chloro(4-chlorophenyl)(1-methyl-1H-imidazol-5-yl)methyl]-6-(3-chlorophenyl)-4H-tetrazolo[1,5-a][1,4]benzodiazepine (described in Example B12a) (0.0015 mol) in THF (10 ml). The mixture was stirred at 5° C. for 1 hour, hydrolized and extracted with CH$_2$Cl$_2$. The organic layer was separated, dried (MgSO$_4$), filtered and the solvent was evaporated till dryness. The residue (0.55 g) was purified by column chromatography over silica gel (eluent: toluene/2-propanol/NH$_4$OH 75/25/0.3; 20–45 μm). The pure fractions were collected and the solvent was evaporated. The residue was crystallized from acetonitrile. The precipitate was filtered off, washed with diethyl ether and dried, yielding 0.18 g (23%) of 6-(3-chlorophenyl)-α-(4-chlorophenyl)-α-(1-methyl-1H-imidazol-5-yl)-4H-tetrazolo[1,5-a][1,4]benzodiazepine-8-methanamine, mp. 218° C.

EXAMPLE B13

A mixture of intermediate (18) (0.015 mol) and MgSO$_4$ (50 g) in toluene (200 ml) was stirred and refluxed overnight and brought to room temperature. The solvent was evaporated. The residue was taken up in DCM and methanol. The mixture was stirred, filtered over celite and washed with DCM. The filtrate was extracted with DCM. The organic layer was separated, washed with K$_2$CO$_3$ 10% and with water, dried (MgSO$_4$), filtered and the solvent was evaporated. The residue (8.5 g) was purified by column chromatography over silica gel (eluent: CH$_2$Cl$_2$/CH$_3$OH/NH$_4$OH 89/10/1; 20–45 μm). The pure fractions were collected and their solvents evaporated yielding 5.3 g (71%) of residue, part of which (1.2 g) was crystallised from acetonitrile and diethyl ether. The precipitate was filtered off and dried in vacuo, yielding 0.9 g (12%) of 5-(3-chlorophenyl)-7-[(4-chlorophenyl)(1-methyl-1H-imidazol-5-yl)methyl]-1,5-dihydro-4,1-benzothiazepin-2(3H)-one, mp. 187° C.

EXAMPLE B14

BuLi 1.6M (31.9 ml) was added dropwise at −70° C. under N$_2$ flow to a mixture of 1-methyl-1H-imidazole (0.051 mol) in THF (85 ml). The mixture was stirred at −70° C. for 30 min. ClSiEt$_3$ (0.051 mol) was added. The mixture was brought slowly to 10° C. and cooled again to −70° C. BuLi 1.6M (31.9 ml) was added dropwise. The mixture was stirred at −70° C. for 1 hour, brought to −20° C., cooled again to −70° C. and added dropwise at −70° C. under N$_2$ flow to a solution of intermediate (21) (0.0231 mol) in THF (100 ml). The mixture was stirred at −70° C. for 5 min, hydrolyzed and extracted with EtOAc. The organic layer was separated, dried, filtered and the solvent was evaporated. The residue (14.5 g) was purified by column chromatography over silica gel (eluent: CH$_2$Cl$_2$/CH$_3$OH/NH$_4$OH 95/5/0.1; 20–45 μm). The pure fractions were collected and the solvent was evaporated, yielding 4.6 g (38%) of 5-(3-chlorophenyl)-7-[(4-chlorophenyl)hydroxy(1-methyl-1H-imidazol-5-yl)methyl]-1,5-dihydro-4,1-benzothiazepine-2(3H)-thione.

EXAMPLE B15 a) Hydrazine (4.5 ml) was added at room temperature to a mixture of 5-(3-chlorophenyl)-7-[(4-chlorophenyl)hydroxy(1-methyl-1H-imidazol-5-yl)methyl]-1,5-dihydro-4,1-benzothiazepine-2(3H)-thione (described in Example B14) (0.0085 mol) in THF (50 ml). The mixture was stirred at room temperature for 30 min, poured out into ice water, saturated with NaCl and extracted with DCM. The organic layer was separated, dried (MgSO$_4$), filtered and the solvent was evaporated till dryness, yielding 4.3 g (96.4%) of 5-(3-chlorophenyl)-α-(4-chlorophenyl)-2-hydrazino-3,5dihydro-α-(1-methyl-1H-imidazol-5-yl)-4,1-benzothiazepine-7-methanol.

b) A mixture of 5-(3-chlorophenyl)-α-(4-chlorophenyl)-2-hydrazino-3,5-dihydro-α-(1-methyl-1H-imidazol-5-yl)-4,1-benzothiazepine-7-methanol (described in Example B15a) (0.0082 mol) in HCl 1N (45 ml) was cooled on an ice bath. A solution of NaNO$_2$ (0.009 mol) in water (12 ml) was added. The mixture was stirred at 5° C. for 30 min. Ice was added. The mixture was basified with K$_2$CO$_3$ 10% and extracted with DCM. The organic, layer was separated, dried (MgSO$_4$), and the solvent was evaporated till dryness. The residue (5 g) was purified by column chromatography over silica gel (eluent: CH$_2$Cl$_2$/CH$_3$OH/NH$_4$OH 96/4/0.1; 20–45 μm). The pure fractions were collected and the solvent was evaporated. The residue was crystallized from CH$_3$CN/2-propanone/DIPE. The precipitate was filtered off and dried, yielding 1 g (23.2%) of 6-(3-chlorophenyl)-α-(4-chlorophenyl)-α-(1-methyl-1H-imidazol-5-yl)-4H,6H-tetrazolo[1,5-a][4,1]benzothiazepine-8-methanol, mp. 217° C.

EXAMPLE B16 a) Tetraphosphorus decasulfide (0.0097 mol) was added at room temperature to a solution of 5-(3-chlorophenyl)-7-[(4-chlorophenyl)(1-methyl-1H-imidazol-5-yl)methyl]-1,5-dihydro-4,1-benzothiazepin-2(3H)-one (see Example B13) (0.0081 mol) in THF (50 ml). The mixture was stirred at room temperature for 2 hours and poured out into ice water. The precipitate was filtered off and taken up in $K_2CO_3$ 10%. The mixture was extracted with DCM and a small amount of methanol. The organic layer was separated, dried, filtered and the solvent was evaporated, yielding 3.2 g (77.5%) of 5-(3-chlorophenyl)-7-[(4-chlorophenyl)(1-methyl-1H-imidazol-5-yl)methyl]-1,5-dihydro-4,1-benzothiazepine-2(3H)-thione.

b) Hydrazine (3.2 ml) was added at room temperature to a mixture of 5-(3-chlorophenyl)-7-[(4-chlorophenyl)(1-methyl-1H-imidazol-5-yl)methyl]-1,5-dihydro-4,1-benzothiazepine-2(3H)-thione (described in Example B16a) (0.0063 mol) in THF (35 ml). The mixture was stirred at room temperature for 30 min, poured out into ice water, saturated with NaCl and extracted with DCM and a small amount of methanol. The organic layer was separated, dried, filtered and the solvent was evaporated, yielding 2.3 g (71.9%) of 5-(3-chlorophenyl)-7-[(4-chlorophenyl)(1-methyl-1H-imidazol-5-yl)methyl]-2-hydrazino-3,5-dihydro-4,1-benzothiazepine.

c) A mixture of 5-(3-chlorophenyl)-7-[(4-chlorophenyl)(1-methyl-1H-imidazol-5-yl)methyl]-2-hydrazino-3,5-dihydro-4,1-benzothiazepine (described in Example B16b) (0.0045 mol) in HCl (34 ml) was cooled on an ice bath. A solution of sodium nitrite (0.005 mol) in water (7 ml) was added. The mixture was stirred at 5° C. for 30 min and at room temperature for 30 min, then poured out on ice, basified with $K_2CO_3$ 10% and extracted with DCM. The organic layer was separated, dried ($MgSO_4$), filtered and the solvent was evaporated till dryness. The residue (2.7 g) was purified by column chromatography over silica gel (eluent: $CH_2Cl_2/CH_3OH/NH_4OH$ 97/3/0.1; 20–45 µm). The pure fractions were collected and the solvent was evaporated. The residue was crystallized from 2-propanone/$CH_3CN$/DIPE. The precipitate was filtered off and dried, yielding 0.44 g (18.9%) of 6-(3-chlorophenyl)-8-[(4-chlorophenyl)(1-methyl-1H-imidazol-5-yl)methyl]-4H,6H-tetrazolo[1,5-a][4,1]benzothiazepine, mp. 162° C.

EXAMPLE B17

Thionyl chloride (1 ml) was added slowly to a mixture of intermediate (22) (0.00456 mol) in THF (15 ml). The mixture was stirred and refluxed for 2.5 hours, poured out on ice and $NH_4OH$ and extracted with DCM. The organic layer was separated, dried ($MgSO_4$), filtered and the solvent was evaporated till dryness. The residue (4 g) was purified by column chromatography over silica gel (eluent: $CH_2Cl_2/CH_3OH/NH_4OH$ 95/5/0.1; 20–45 µm). The pure fractions were collected and the solvent was evaporated. The residue was crystallized from $CH_3CN$ and diethyl ether. The precipitate was filtered off and dried in vacuo. The residue was recrystallized from $CH_3CN$ and diethyl ether. The precipitate was filtered off and dried in vacuo, yielding 0.08 g (3%) of 6-(3-chlorophenyl)-8-[(4-chlorophenyl)(1-methyl-1H-imidazol-5-yl)methyl]-1,3,4,6-tetrahydro-2H-5,1-benzothiazocin-2-one, mp. 199° C.

EXAMPLE B18

A mixture of intermediate (29) (0.0125 mol), 1H-imidazole (0.0375 mol) and $K_2CO_3$ (8.62 g) in acetonitrile (150 ml) was stirred and refluxed for 3 h. The mixture was cooled, filtered off and the filtrate was evaporated till dryness. The residue was taken up in DCM. The organic layer was washed with water, dried ($MgSO_4$), filtered off and evaporated. The residue (5.7 g) was purified by column chromatography over silica gel (eluent: $CH_2Cl_2/CH_3OH/NH_4OH$ 97/3/0.1) (15–40 µm). The pure fractions were collected and evaporated. The residue (2.71 g) was crystallized from DIPE, yielding 2.38 g (51%) of (±)-7-[(4-chlorophenyl)-1H-imidazol-1-ylmethyl]-1,3-dihydro-5-phenyl-2H-1,4-benzodiazepin-2-one, mp. 144° C.

EXAMPLE B19 a) A mixture of 6-(3-chlorophenyl)-α-(4-chlorophenyl)-α-(1-methyl-1H-imidazol-5-yl)-4H,6H-tetrazolo[1,5-a][4,1]benzothiazepine-8-methanol (described in Example B15b) (0.0032 mol) in thionyl chloride (40 ml) was stirred at room temperature for 30 min and at 40° C. for 1 hour. The solvent was evaporated till dryness. The product was used without further purification, yielding (quant.) of 8-[chloro(4-chlorophenyl)(1-methyl-1H-imidazol-5-yl)methyl]-6-(3-chlorophenyl)-4H,6H-tetrazolo[1,5-a][4,1]benzothiazepine.

b) 2-propanol/$NH_3$ (50 ml) was added dropwise at 5° C. to a mixture of 8-[chloro(4-chlorophenyl)(1-methyl-1H-imidazol-5-yl)methyl]-6-(3-chlorophenyl)-4H,6H-tetrazolo[1,5-a][4,1]benzothiazepine (described in Example B19a) (0.0032 mol) in THF (50 ml). The mixture was stirred at 5° C. for 30 min, poured out into water and extracted with DCM. The organic layer was separated, dried ($MgSO_4$), filtered and the solvent was evaporated till dryness. The residue (2.5 g) was purified by column chromatography over silica gel (eluent: toluene/2-propanol/$NH_4OH$ 85/15/0.1; 20–45 µm). Two pure fractions were collected and their solvents were evaporated, yielding: 0.29 g F1 (16.9%) and 0.33 g F2 (19.3%). Both fractions were crystallized from $CH_3CN$/DIPE. The precipitate was filtered off and dried, yielding: 0.19 g (11.1%) of (A)-6-(3-chlorophenyl)-α-(4-chlorophenyl)-α-(1-methyl-1H-imidazol-5-yl)-4H,6H-tetrazolo[1,5-a][4,1]benzothiazepine-8-methanamine, melting point 218° C. and 0.17 g (9.9%) of (B)-6-(3-chlorophenyl)-α-(4-chlorophenyl)-α-(1-methyl-1H-imidazol-5-yl)-4H,6H-tetrazolo[1,5-a][4,1]benzothiazepine-8-methanamine, mp.167° C.

EXAMPLE B20 nBuLi (0.009 mol) was added dropwise at −70° C. to a mixture of 3-bromo-pyridine (0.009 mol) in diethyl ether (10 ml) under $N_2$ flow. The mixture was stirred at −70° C. for 15 minutes. A suspension of intermediate (31) (0.003 mol) in THF (30 ml) was added dropwise at −70° C. The mixture was stirred at −70° C. for 1 hour, then brought slowly to room temperature, stirred overnight and poured out into ice water. EtOAc was added. The mixture was extracted with EtOAc. The organic layer was separated, dried ($MgSO_4$), filtered, and the solvent was evaporated. The residue was purified by column chromatography over silica gel (eluent: $CH_2Cl_2/CH_3OH/NH_4OH$ 95/5/0.2; 15–40 µm). The pure fractions were collected and the solvent was evaporated, yielding 0.12 g (7%). This fraction was taken up in diethyl ether. The precipitate was filtered off and dried in a vacuum, yielding 0.1 g (6%) of 6-(3-chlorophenyl)-α-(4-chlorophenyl)-α-(3-pyridinyl)-4H,6H-tetrazolo[1,5-a][4,1]benzothiazepine-8-methanol, MS (MH+) m/e: 532, 534, 536.

EXAMPLE B21

Sodium hydride (0.0016 mol, 60% in oil) was added portionwise at 10° C. to a mixture of 5-(3-chlorophenyl)-7-[(4-chlorophenyl)hydroxy(1-methyl-1H-imidazol-5-yl)methyl]-1,5-dihydro-4,1-benzothiazepin-2(3H)-one (0.0013 mol), obtained in Example B2, in DMF (7 ml). The mixture was stirred for 30 minutes. (Bromomethyl)-cyclopropane (0.0016 mol) was added. The mixture was brought to room temperature, then stirred for 3 hours, poured out into ice water and stirred again for 30 minutes. The precipitate was filtered and taken up in DCM. The organic layer was separated, dried (MgSO$_4$), filtered, and the solvent was evaporated. The residue (0.6 g) was purified by column chromatography over kromasil (eluent: CH$_2$Cl$_2$/CH$_3$OH/NEt$_3$ 97/3/0.1; 10 μm). The pure fractions were collected and the solvent was evaporated. The residue (0.16 g) was crystallized from acetonitrile. The precipitate was filtered off and dried, yielding 0.13 g (17%) of 5-(3-chlorophenyl)-7-[(4-chlorophenyl)hydroxy(1-methyl-1H-imidazol-5-yl)methyl]-1-(cyclopropylmethyl)-1,5-dihydro-4,1-benzothiazepin-2(3H)-one, mp. 245° C.

EXAMPLE B22

2,2,2-trichloroethyl ester carbonochloridic acid (0.0008 mol) was added at room temperature to a mixture of 7-[amino(4-chlorophenyl)(1-methyl-1H-imidazol-5-yl)methyl]-5-(3-chlorophenyl)-1,5-dihydro-1-methyl-4,1-benzothiazepin-2(3H)-one (0.0001 mol), obtained in example B11b, in DMF (2 ml). The mixture was stirred at room temperature for 3 days and poured out into ice water. The precipitate was filtered off and dried, yielding 0.02 g. The aqueous layer was extracted with EtOAc. The organic layer was washed with water, separated, dried (MgSO$_4$), filtered and the solvent was evaporated, yielding 0.045 g. This fraction was purified by column chromatography over kromasil (eluent: CH$_2$Cl$_2$/CH$_3$OH 96/4; 5 μm). The pure fractions were collected and the solvent was evaporated, yielding 0.007 g (7%) of N'-[(E)-(4-chlorophenyl)[5-(3-chlorophenyl)-1,2,3,5-tetrahydro-1-methyl-2-oxo-4,1-benzothiazepin-7-yl](1-methyl-1H-imidazol-5-yl)methyl]-N,N-dimethyl-methanimidamide, MS (MH+) m/e: 578 580, 582.

The following compounds were prepared analogous to the one of the above examples (the example number analogous to which they were prepared is indicated between square brackets after the compound number).

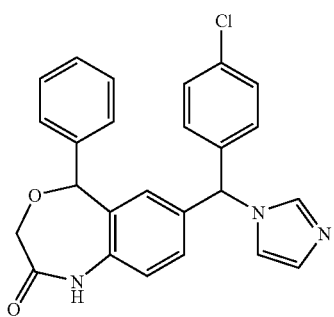

[B18] mp. 175° C.

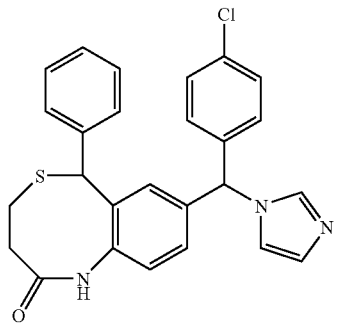

[B18] mp. 190° C.

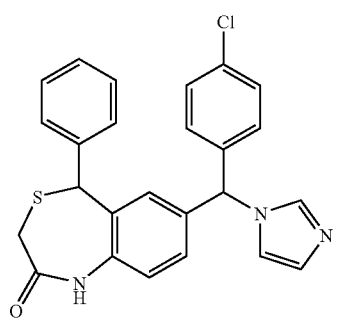

[B18] mp. 130° C.

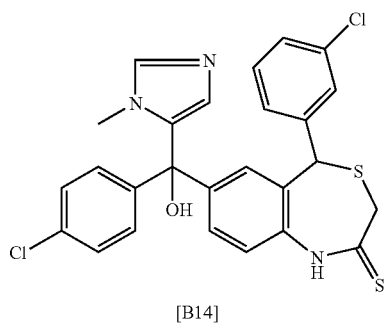

[B14]

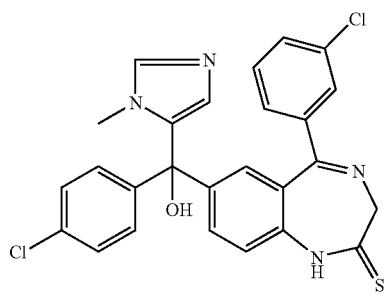

[B5] mp. 196° C.

-continued

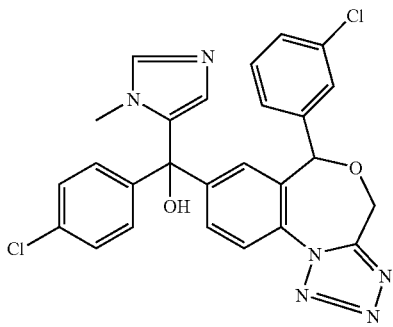

[B5] mp. 143° C.

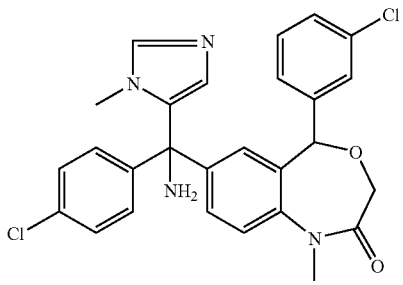

[B10], mp. 152° C.

C. Pharmacological Example.

EXAMPLE C.1

"In Vitro Assay for Inhibition of Farnesyl Protein Transferase"

An in vitro assay for inhibition of farnesyl transferase was performed essentially as described in WO 98/40383, pages 33–34.

EXAMPLE C.2

"Ras-Transformed Cell Phenotype Reversion Assay"

The ras-transformed cell phenotype reversion assay was performed essentially as described in WO 98/40383, pages 34–36.

EXAMPLE C.3

"Farnesyl Protein Transferase Inhibitor Secondary Tumor Model"

The farnesyl protein transferase inhibitor secondary tumor model was used as described in WO 98/40383, page 37.

D. Composition Example: Film-Coated Tablets
Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I):

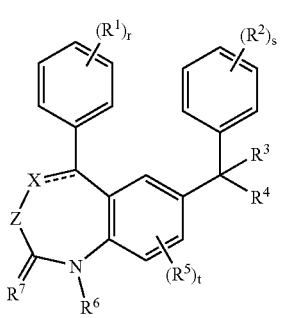

or a pharmaceutically acceptable salt or N-oxide or stereochemically isomeric form thereof, wherein
the dotted line represents an optional bond;
r and s are each independently 0, 1, 2, 3, 4 or 5;
t is 0, 1, 2 or 3;
X is —NH—, —O—, or —S— (when the optional bond represented by the dotted line is absent) or —N= (when the optional bond represented by the dotted line is present);
Z is $C_{1-2}$ alkanediyl which may be optionally substituted by one or more substituents independently selected from $C_{1-4}$alkyl (optionally substituted by hydroxy), aryl $C_{1-4}$alkyl, $C_{1-4}$alkyloxy$C_{1-4}$alkyl, hydroxy$C_{1-4}$alkyl, amino$C_{1-4}$alkyl, mono or dialkylamino$C_{1-4}$alkyl, $C_{1-4}$alkylthio$C_{1-4}$alkyl or aryl;
each $R^1$ and $R^2$ is independently azido, hydroxy, halo, cyano, nitro, $C_{1-6}$alkyl, —$(CR^{20}R^{21})_p$—$C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}$S $C_{1-6}$alkyl, trihalomethyl, aryl$C_{1-6}$alkyl, Het$^2$$C_{1-6}$alkyl, —$C_{1-6}$alkyl-$NR^{22}R^{23}$, —$C_{1-6}$alkyl$NR^{22}$$C_{1-6}$alkyl-$NR^{22}R^{23}$, —$C_{1-6}$alkyl$NR^{22}$-Het$^2$, —$C_{1-6}$alkyl-$NR^{22}$—$C_{1-6}$alkyloxy$C_{1-6}$alkyl, —$C_{1-6}$alkyl$NR^{22}$—$C_{1-6}$alkyl-S—$C_{1-6}$alkyl-Ar$^2$, —$C_{1-6}$alkyl$NR^{22}$—$C_{1-6}$alkyl-S—$C_{1-6}$alkyl, —$C_{1-6}$alkyl$NR^{22}$$C_{1-6}$alkyl-Ar$^2$ (in which the $C_{1-6}$alkyl moiety adjacent to the Ar$^2$ is optionally substituted by $C_{1-6}$alkyloxycarbonyl), —$C_{1-6}$alkyl$NR^{22}$$C_{1-6}$alkyl-Het$^2$, —$C_{1-6}$alkyl$NR^{22}$CO$C_{1-6}$alkyl, —$C_{1-6}$alkyl$NR^{22}$COAlkAr$^2$, —$C_{1-6}$alkyl$NR^{22}$COAr$^2$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, —OC$_{1-6}$alkyl-$NR^{22}R^{23}$, trihalomethoxy, aryl$C_{1-6}$alkyloxy, Het$^2$$C_{1-6}$alkyloxy, $C_{1-6}$alkylthio, $C_{2-6}$alkenyl, cyano$C_{2-6}$alkenyl, —$C_{2-6}$alkenyl-$NR^{22}R^{23}$, hydroxycarbonyl$C_{2-6}$alkenyl, $C_{1-6}$alkyloxycarbonyl$C_{2-6}$alkenyl, $C_{2-6}$alkynyl, —CHO, $C_{1-6}$alkylcarbonyl, hydroxy$C_{1-6}$alkylcarbonyl, $C_{1-4}$alkyloxycarbonyl, —$CONR^{22}R^{23}$, —$CONR^{22}$—$C_{1-6}$alkyl-$NR^{22}R^{23}$, —$CONR^{22}$—$C_{1-6}$alkyl-$Het^2$, —$CONR^{22}$—$C_{1-6}$alkyl-$Ar^2$, —$CONR^{22}$-$Het^2$, —$CONR^{22}Ar^2$, —$CONR^{22}$—O—$C_{1-6}$alkyl, —$CONR^{22}$—$C_{1-6}$alkenyl, —$NR^{22}R^{23}$, —$OC(O)R^{24}$, —$CR^{24}$=$NR^{25}$, —$CR^{24}$=N—$OR^{25}$, —$NR^{24}C(O)NR^{22}R^{23}$, —$NR^{24}SO_2R^{25}$, —$NR^{24}C(O)R^{25}$, —$S(O)_{0-2}R^{24}$, —$SO_2NR^{24}R^{25}$, —$C(NR^{26}R^{27})$=$NR^{28}$; —$Sn(R^{24})_3$, —$SiR^{24}R^{24}R^{25}$, —$B(OR^{24})_2$, —$P(O)OR^{24}OR^{25}$, $Ar^2$oxy, $Het^2$-oxy, or a group of formula -Z, —CO-Z or —CO—$NR^y$-Z in which $R^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, —$COOR^{24}$, aminocarbonyl, $C_{1-6}$alkylthio, hydroxy, —$NR^{22}R^{23}$, $C_{1-6}$alkylsulphonylamino, $C_{1-6}$alkyl, halo$C_{1-6}$alkyl,$C_{1-6}$alkyloxy or phenyl; or two $R^1$ or $R^2$ substituents adjacent to one another on the phenyl ring may form together a bivalent radical of formula —O—$CH_2$—O— (a-1)

—O—$CH_2$—$CH_2$—O— (a-2)

—O—CH=CH— (a-3)

—O—$CH_2$—$CH_2$— (a-4)

—O—$CH_2$—$CH_2$—$CH_2$— (a-5)

—CH=CH—CH=CH— (a-6)

p is 0 to 5;

$R^{20}$ and $R^{21}$ are independently hydrogen or $C_{1-6}$ alkyl and are independently defined for each iteration of p in excess of 1;

$R^{22}$ and $R^{23}$ are independently hydrogen, $C_{1-6}$ alkyl or —$(CR^{20}R^{21})_p$—$C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, $OCF_3$, hydroxycarbonyl, $C_{1-6}$alkyloxycarbonyl, aminocarbonyl, mono- or di-($C_{1-6}$alkyl)aminocarbonyl, amino, mono- or di($C_{1-6}$alkyl) amino, $C_{1-6}$alkylsulfonylamino, oxime, or phenyl;

$R^{24}$ and $R^{25}$ are independently hydrogen, $C_{1-6}$ alkyl, —$CR_{20}R_{21}$p-$C_{3-10}$cycloalkyl or aryl$C_{1-6}$alkyl;

$R^{26}$, $R^{27}$ and $R^{28}$ are independently hydrogen and $C_{1-6}$alkyl or $C(O)$ $C_{1-6}$alkyl;

$R^3$ is hydrogen, halo, cyano, $C_{1-6}$alkyl, —$(CR^{20}R^{21})_p$—$C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, aryl$C_{1-6}$alkyloxy$C_{1-6}$alkyl,$C_{1-6}$alkylthio$C_{1-6}$alkyl, hydroxycarbonyl$C_{1-6}$alkyl, $C_{1-6}$alkylcarbonyl$C_{1-6}$alkyl, $C_{1-6}$alkyloxycarbonyl$C_{1-6}$alkyl, —$C_{1-6}$alkyl-$NR^{22}R^{23}$, —$C_{1-6}$alkyl-$CONR^{22}R^{23}$, aryl$C_{1-6}$alkyl, $Het^2C_{1-6}$alkyl, $C_{2-6}$alkenyl, —$C_{2-6}$alkenyl $NR^{22}R^{23}$, $C_{2-6}$alkynyl, hydroxycarbonyl, $C_{1-6}$alkyloxycarbonyl, aryl, or $Het^2$; or a radical of formula —O—$R^{10}$ (b-1)

—S—$R^{10}$ (b-2)

—$NR^{11}R^{12}$ (b-3)

or

—N=$CR^{10}R^{11}$ (b-4)

wherein $R^{10}$ is hydrogen, $C_{1-6}$alkyl, —$C(CR^{20}R^{21})_p$—$C_{3-10}$cycloalkyl, aryl$C_{1-6}$alkyl, $C_{2-6}$alkenyl, $C_{2-6}$alkynyl, $C_{1-6}$alkylcarbonyl, aryl, a group of formula —$NR^{22}R^{23}R$ or —$C_{1-6}$alkylC(O)O$C_{1-6}$alkyl $NR^{22}R^{23}$, or a radical of formula -Alk-$OR^{13}$ or -Alk-$NR^{14}R^{15}$;

$R^{11}$ is hydrogen, $C_{1-6}$alkyl, —$(CR^{20}R^{21})_p$—$C_{3-10}$cycloalkyl, $C_{2-6}$alkenyl, $C_{2-6}$alkynyl, aryl or aryl$C_{1-6}$ alkyl;

$R^{12}$ is hydrogen, hydroxy, $C_{1-6}$alkyl, —$(CR^{20}R^{21})_p$—$C_{3-10}$cycloalkyl, $C_{1-6}$alkylcarbonyl$C_{1-6}$alkyl, aryl$C_{1-6}$alkyl,$C_{2-6}$alkenyl, $C_{2-6}$alkynyl, aryl, $C_{1-6}$alkyloxy, a group of formula —$NR^{22}R^{23}$, $C_{1-6}$alkylcarbonylamino, $C_{1-6}$alkylcarbonyl, halo$C_{1-6}$alkylcarbonyl, aryl$C_{1-6}$alkylcarbonyl, $Het^2C_{1-6}$alkylcarbonyl, arylcarbonyl, $C_{1-6}$alkyloxycarbonyl, trihalo$C_{1-6}$alkyloxycarbonyl, $C_{1-6}$alkyloxy$C_{1-6}$alkylcarbonyl, aminocarbonyl, mono- or di($C_{1-6}$alkyl)aminocarbonyl wherein the alkyl moiety may optionally be substituted by one or more substituents independently selected from aryl and $C_{1-6}$alkyloxycarbonyl substituents; aminocarbonylcarbonyl, mono- or di($C_{1-6}$alkyl)amino$C_{1-6}$alkylcarbonyl, or a radical of formula -Alk-$OR^{13}$ or Alk-$NR^{14}R^{15}$;

wherein Alk is $C_{1-6}$alkanediyl;

$R^{13}$ is hydrogen, $C_{1-6}$alkyl, —$(CR^{20}R^{21})_p$—$C_{3-10}$cycloalkyl, $C_{2-6}$alkenyl, $C_{2-6}$alkynyl, $C_{1-6}$alkylcarbonyl, hydroxy$C_{1-6}$alkyl, aryl or aryl$C_{1-6}$alkyl;

$R^{14}$ is hydrogen,$C_{1-6}$alkyl, —$(CR^{20}R^{21})_p$—$C_{3-10}$cycloalkyl, $C_{2-6}$alkenyl, $C_{2-6}$alkynyl, aryl or aryl$C_{1-6}$ alkyl;

$R^{15}$ is hydrogen, $C_{1-6}$alkyl, —$(CR^{20}R^{21})_p$—$C_{3-10}$cycloalkyl, $C_{2-6}$alkenyl, $C_{2-6}$alkynyl, $C_{1-6}$alkylcarbonyl, aryl or aryl$C_{1-6}$alkyl;

$R^4$ is a radical of formula

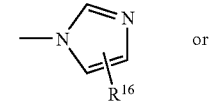

(c-1)

or

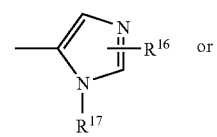

(c-2)

or

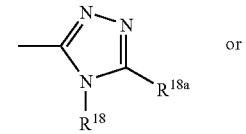

(c-3)

or

-continued

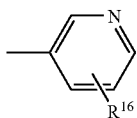
(c-4)

wherein $R^{16}$ is hydrogen, halo, $C_{1-6}$alkyl, $-(CR^{20}R^{21})_p-C_{3-10}$cycloalkyl, hydroxy$C_{1-6}$alkyl, $C_{1-6}$alkyloxy$C_{1-6}$alkyl, $C_{1-6}$alkylS(O)$_{0-2}C_{1-6}$alkyl, $C_{1-6}$alkyloxy, $C_{1-6}$alkylthio, a group of formula $-NR^{22}R^{23}$, hydroxycarbonyl, $C_{1-6}$alkyloxycarbonyl or aryl, $R^{17}$ is hydrogen, $C_{1-6}$alkyl, $-(CR^{20}R^{21})_p-C_{3-10}$cycloalkyl, hydroxy$C_{1-6}$alkyl, $C_{1-6}$alkyloxy$C_{1-6}$alkyl, aryl $C_{1-6}$alkyl, trifluoromethyl, trifluoromethyl$C_{1-6}$alkyl, hydroxycarbonyl$C_{1-6}$alkyl, $C_{1-6}$alkyloxycarbonyl$C_{1-6}$alkyl, mono- or di$_{(1-6}$alkyl)aminosulphonyl or $-C_{1-6}$alkyl P(O)OR$^{24}$OR$^{25}$;

$R^{18}$ is hydrogen, $C_{1-6}$alkyl, $-(CR^{20}R^{21})_p-C_{3-10}$cycloalkyl, aryl$C_{1-6}$alkyl or $C_{1-6}$alkyloxy$C_{1-6}$alkyl;

$R^{18a}$ is hydrogen, $-SH$ or $-SC_{1-4}$alkyl;

$R^5$ is cyano, hydroxy, halo, $C_{1-6}$alkyl, $-(CR^{20}R^{21})_p-C_{3-10}$cycloalkyl, $C_{2-6}$alkenyl, $C_{2-6}$alkynyl, $C_{1-6}$alkyloxy, aryl$C_{1-6}$alkyloxy, Het$^2C_{1-6}$alkyloxy, hydroxycarbonyl, $C_{1-6}$alkyloxycarbonyl, or a group of formula $-NR^{22}R^{23}$ or $-CONR^{22}R^{23}$;

$R^6$ is hydrogen, $C_{1-6}$alkyl, $-CF_3$, $-(CR^{20}R^{21})_p-C_{3-10}$cycloalkyl, cyano$C_{1-6}$alkyl, $-C_{1-6}$alkylCO$_2R^{24}$, aminocarbonyl$C_{1-6}$alkyl or $-C_{1-6}$alkyl-NR$^{22}R^{23}$, $R^{24}SO_2$, $R^{24}SO_2C_{1-6}$alkyl, $-C_{1-6}$alkyl-OR$^{24}$, $-C_{1-6}$alkyl-SR$^{24}$, $-C_{1-6}$alkylCONR$^{22}-C_{1-6}$alkyl-NR$^{22}R^{23}$, $-C_{1-6}$alkylCONR$^{22}-C_{1-6}$alkyl-Het$^2$, $-C_{1-6}$alkyl CONR$^{22}-C_{1-6}$alkyl-Ar$^2$, $-C_{1-6}$alkyl CONR$^{22}$-Het$^2$, $-C_{1-6}$alkyl CONR$^{22}$Ar$^2$, $-C_{1-6}$alkyl CONR$^{22}-O-C_{1-6}$alkyl, $-C_{1-6}$alkyl CONR$^{22}-C_{1-6}$alkenyl, -Alk-Ar$^2$ or -AlkHet$^2$;

$R^7$ is oxygen or sulphur; or $R^6$ and $R^7$ together form a trivalent radical of formula:

| | |
|---|---|
| $-CR^{30}=CR^{31}-N=$ | (x-1) |
| $-CR^3=N-N=$ | (x-2) |
| $-C(=O)-NH-N=$ | (x-3) |
| $-N=N-N=$ | (x-4) |
| $-N=CR^{30}-N=$ | (x-5) |
| $-CR^{30}=CR^{31}-CR^{32}=$ | (x-6) |
| $-CR^{30}=N-CR^{31}=$ | (x-7) |
| $-C(=O)-NH-CR^{30}=$ | (x-8) |
| $-N=N-CR^{30}=$ | (x-9) or |
| $-CH_2-(CH_2)_{0-1}-CH_2-N=$ | (x-10) | wherein each $R^{30}$, $R^{31}$ and $R^{32}$ are independently hydrogen, $C_{1-6}$ alkyl, $-OR^{24}$, $-COOR^{24}$, $-NR^{22}R^{23}$, $-C_{1-6}$alkylOR$^{24}$, $-C_{1-6}$ alkylSR$^{24}$, $R^{23}R^{22}NC_{1-6}$alkyl-, $-CONR^{22}R^{23}$, $C_{2-6}$alkenyl, $C_{2-6}$alkenylAr$^2$, $C_{2-6}$alkenylHet$^2$, cyano, amino, thio, $C_{1-6}$ alkylthio, $-O-Ar^2$, $-S-Ar^2$ or Ar$^2$;

Ar$^2$ is phenyl, naphthyl or phenyl or naphthyl substituted by one to five substituents each independently selected from halo, hydroxy, cyano, nitro, $C_{1-6}$alkyl, halo$C_{1-6}$alkyl, -alkylNR$^{22}R^{23}$, $C_{1-6}$alkyloxy, OCF$_3$, hydroxycarbonyl, $C_{1-6}$alkyloxycarbonyl, aryloxy, $-NR^{22}R^{23}$, $C_{1-6}$alkylsulfonylamino, oxime or phenyl, or a bivalent substituent of formula $-O-CH_2-O-$ or $O-CH_2-CH_2-O-$;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkylNR$^{22}R^{23}$, $C_{1-6}$alkyloxy, OCF$_3$, hydroxycarbonyl, $C_{1-6}$alkyloxycarbonyl, $-CONR^{22}R^{23}$, $-NR^{22}R^{23}$, $C_{1-6}$alkylsulfonylamino, oxime or phenyl.

2. A compound according to claim 1 in which:

r and s are each independently 0, 1 or 2;

t is 0 or 1;

Z is $C_{1-2}$ alkanediyl;

$R^1$ is halo, $C_{1-6}$alkyl, $-(CR^{20}R^{21})_p-C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, $C_{1-6}$alkylthio, hydroxycarbonyl, $C_{1-6}$alkyloxycarbonyl, $-CONR^{22}R^{23}$, or $-CH=NOR^{25}$; or two $R^1$ substituents adjacent to one another on the phenyl ring may independently form together a bivalent radical of formula

| | |
|---|---|
| $-O-CH_2-O-$ | (a-1) |
| $-O-CH_2-CH_2-O-$ | (a-2) |

$R^2$ is halo, cyano, nitro, $C_{1-6}$alkyl, cyano$C_{1-6}$alkyl, $-C_{1-6}$alkyl NR$^{22}R^{23}$; cyano$C_{2-6}$alkenyl, $-NR^{22}R^{23}$, CHO, $-CR^{24}=N-OR^{25}$, $C_{1-6}$alkyloxycarbonyl, $-CONR^{22}R^{23}$; or two $R^2$ substituents adjacent to one another on the phenyl ring may independently form together a bivalent radical of formula

| | |
|---|---|
| $-O-CH_2-O-$ | (a-1) |
| $-O-CH_2-CH_2-O-$ | (a-2) |

$R^3$ is hydrogen, $C_{1-6}$alkyl, $-(CR^{20}R^{21})_p-C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, $-C_{1-6}$alkyl NR$^{22}R^{23}$, Het$^2C_{1-6}$alkyl, $-C_{2-6}$alkenyl NR$^{22}R^{23}$, or -Het$^2$; or a group of formula

| | |
|---|---|
| $-O-R^{10}$ | (b-1) |
| $-NR^{11}R^{12}$ | (b-3) | wherein $R^{10}$ is hydrogen, $C_{1-6}$alkyl, or $-(CR^{20}R^{21})_p-C_{3-10}$cycloalkyl, or a group of formula -Alk-OR$^{13}$ or -Alk-NR$^{14}R^{15}$;

$R^{11}$ is hydrogen or $C_{1-6}$alkyl;

$R^{12}$ is hydrogen, hydroxy, $C_{1-6}$alkyl, $-(CR^{20}R^{21})_p-C_{3-10}$cycloalkyl, $C_{1-6}$alkyloxy, $C_{1-6}$alkylcarbonyl, aryl$C_{1-6}$alkylcarbonyl, Het$^2C_{1-6}$alkylcarbonyl, aminocarbonyl, or a radical of formula -Alk-OR$^{13}$ or Alk-NR$^{14}R^{15}$;

wherein Alk is $C_{1-6}$alkanediyl;

$R^{13}$ is hydrogen, $C_{1-6}$alkyl or $-(CR^{20}R^{21})_p-C_{3-10}$cycloalkyl;

$R^{14}$ is hydrogen, $C_{1-6}$alkyl, or $-(CR^{20}R^{21})_p-C_{3-10}$cycloalkyl;

$R^{15}$ is hydrogen or $C_{1-6}$alkyl;

R⁴ is a radical of formula (c-2) or (c-3)
wherein R¹⁶ is hydrogen, halo or $C_{1-6}$alkyl,
R¹⁷ is hydrogen, $C_{1-6}$alkyl, —$(CR^{20}R^{21})_p$—$C_{3-10}$cycloalkyl, $C_{1-6}$alkyloxy$C_{1-6}$alkyl or trifluoromethyl;
R¹⁸ is hydrogen, $C_{1-6}$alkyl or —$(CR^{20}R^{21})_p$—$C_{3-10}$cycloalkyl;
R¹⁸ᵃ is hydrogen;
R⁵ is cyano, halo, $C_{1-6}$alkyl, $C_{2-6}$alkynyl, $C_{1-6}$alkyloxy or $C_{1-6}$allyloxycarbonyl:
R⁶ is is hydrogen, $C_{1-6}$alkyl, —$C_{1-6}$alkyl$CO_2R^{24}$, —$C_{1-6}$alkyl-$C(O)NR^{22}R^{23}$, -Alk-Ar², -AlkHet² or —$(CR^{20}R^{21})_p$—$C_{3-10}$cycloalkyl,
R⁷ is oxygen or sulphur; or R⁶ and R⁷ together form a trivalent radical of formula (x-1), (x-2), (x-3), (x-4) or (x-9);
Het² is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

3. A compound according to claim 1 in which:
Z is $C_{1-2}$ alkanediyl;
r is 0, 1 or 2;
s is 0 or 1;
t is 0;
R¹ is halo, $C_{1-6}$alkyl, $C_{2-6}$alkenyl, $C_{2-6}$alkynyl or two R¹ substituents ortho to one another on the phenyl ring may independently form together a bivalent radical of formula (a-1);
R² is halo, cyano, nitro, CHO, —$CR^{24}$=N—$OR^{25}$ in which R²⁴ is hydrogen and R²⁵ is hydrogen or $C_{1-6}$alkyl, or two R² substituents ortho to one another on the phenyl ring may independently form together a bivalent radical of formula (a-1);
R³ is Het² or a group of formula (b-1) or (b-3) wherein R¹⁰ is hydrogen or a group of formula -Alk-OR¹³.
R¹¹ is hydrogen;
R¹² is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;
Alk is $C_{1-6}$alkanediyl and R¹³ is hydrogen;
R⁴ is a group of formula (c-2) or (c-3) wherein
R¹⁶ is hydrogen, halo or $C_{1-6}$alkyl;
R¹⁷ is hydrogen or $C_{1-6}$alkyl;
R¹⁸ is hydrogen or $C_{1-6}$alkyl;
R¹⁸ᵃ is hydrogen;
R⁶ is hydrogen, —$(CR^{20}R^{21})_p$—$C_{3-10}$cycloalkyl, —$C_{1-6}$alkyl$CO_2R^{24}$, aminocarbonyl$C_{1-6}$alkyl, -Alk-Ar² or -AlkHet² or $C_{1-6}$alkyl;
R⁷ is oxygen or sulphur; or R⁶ and R⁷ together form a trivalent radical of formula (x-1), (x-2), (x-3), (x-4) or (x-9) and aryl is phenyl.

4. A compound according to claim 1 in which:
Z is $C_{1-2}$ alkanediyl,
r is 0 or 1;
s is 1;
t is 0;

R¹ is halo, $C_{1-6}$alkyl or forms a bivalent radical of formula (a-1);
R² is halo, cyano or $C_{1-6}$alkyl;
R³ is hydrogen or a radical of formula (b-1) or (b-3);
R¹⁰ is hydrogen or -Alk-OR¹³
R¹¹ is hydrogen;
R¹² is hydrogen or $C_{1-6}$alkylcarbonyl;
R¹³ is hydrogen;
R⁴ is a radical of formula (c-2) or (c-3);
R¹⁶ is hydrogen;
R¹⁷ is $C_{1-6}$alkyl;
R¹⁸ is $C_{1-6}$alkyl;
R¹⁸ᵃ is hydrogen;
R⁶ is hydrogen, $C_{1-6}$alkyl, —$CH_2$—$C_{3-10}$cycloalkyl, —$C^{1-6}$alkyl$CO_2R^{24}$ (wherein R²⁴ is H, or ethyl), aminocarbonyl$C_{1-6}$alkyl, -Alk-Ar² or -AlkHet²; and
R⁷ is oxygen or sulphur; or R⁶ and R⁷ together form a trivalent radical of formula (x-2), (x-3) or (x-4).

5. A compound according to claim 1 in which: Z is $C_{1-2}$ alkanediyl, r is 0 or 1, s is 1, t is 0, R¹ is halo R² is halo or cyano, R³ is hydrogen or a radical of formula (b-1) or (b-3), R⁹ is hydrogen, R¹⁰ is hydrogen, R¹¹ is hydrogen and R¹² is hydrogen, R⁴ is a radical of formula (c-2) or (c-3), wherein R¹⁶ is hydrogen, R¹⁷ is $C_{1-6}$alkyl, R¹⁸ is $C_{1-6}$alkyl, R¹⁸ᵃ is hydrogen; R⁶ is hydrogen, $C_{1-6}$alkyl,
—$CH_2$—$C_{3-10}$cycloalkyl or-$C_{1-6}$alkylAr² and R⁷ is oxygen or sulphur, or R⁶ and R⁷ together form a trivalent radical of formula (x-2) or (x-4).

6. A compound according to claim 1 in which: X is —S—, Z is —$CH_2$—, r and s are 1, t is 0, R¹ is halo, R² is halo or cyano, R³ is a radical of formula (b-1) or (b-3), R⁹ is hydrogen, R¹⁰ and R¹¹ are hydrogen and R¹² is hydrogen, R⁴ is a radical of formula (c-2) or (c-3), R¹⁶ is hydrogen, R¹⁷ is $C_{1-6}$alkyl, R¹⁸ is $C_{1-6}$alkyl, R¹⁸ᵃ is hydrogen; R⁶ is hydrogen, $C_{1-6}$alkyl, —$CH_2$—$C_{3-10}$cycloalkyl or -alkylAr² and R⁷ is oxygen or sulphur; or R⁸ and R⁷ together form a trivalent radical of formula(x-4).

7. A compound according to claim 1 selected from:
5-(3-chlorophenyl)-7-[(4-chlorophenyl)hydroxy(1-methyl-1H-imidazol-5-yl)methyl]-1,5-dihydro-1-methyl-4,1-benzoxazepin-2(3H)-one,
5-(3-chlorophenyl)-7-[(4-chlorophenyl)hydroxy(1-methyl-1H-imidazol-5-yl)methyl]-1,5-dihydro-1-methyl-4,1-benzothiazepin-2(3H)-one,
5-(3-chlorophenyl)-7-[(4-chlorophenyl)hydroxy(1-methyl-1H-imidazol-5-yl)methyl]-1,5-dihydro-4,1-benzoxazepine-2(3H)-thione,
7-[amino(4-chlorophenyl)(1-methyl-1H-imidazol-5-yl)methyl]-5-(3-chlorophenyl)-1,5-dihydro-1-methyl-4,1-benzothiazepin-2(3H)-one,
6-(3-chlorophenyl)-α-(4-chlorophenyl)-α-(1-methyl-1H-imidazol-5-yl)-4H-tetrazolo[1,5-a][1,4]benzodiazepine-8-methanamine,
5-(3-chlorophenyl)-7-[(4-chlorophenyl)(1-methyl-1H-imidazol-5-yl)methyl]-1,5-dihydro-4,1-benzothiazepin-2(3H)-one,
(B)-6-(3-chlorophenyl)-α-(4-chlorophenyl)-α-(1-methyl-1H-imidazol-5-yl)-4H,6H-tetrazolo[1,5-a][4,1]benzothiazepine-8-methanamine,
6-(3-chlorophenyl)-8-[(4-chlorophenyl)(1-methyl-1H-imidazol-5-yl)methyl]-4H,6H-tetrazolo[1,5-a][4,1] benzothiazepine,
6-(3-chlorophenyl)-8-[(4-chlorophenyl)(1-methyl-1H-imidazol-5-yl)methyl]-1,3,4,6-tetrahydro-2H-5,1-benzothiazocin-2-one
and their pharmaceutically acceptable salts.

8. A process for the preparation of a compound as claimed in claim 1 which comprises:
a) cyclising a compound of formula (II):

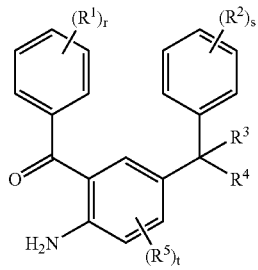

to form a compound of formula (I) in which $R^6$ is hydrogen and $R^7$ is oxygen; or
b) reacting a compound of formula (III):

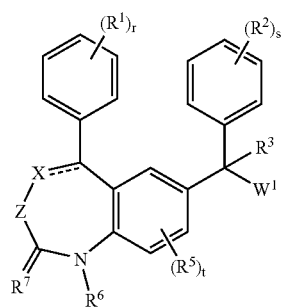

in which $W^1$ is a replaceable group, with an imidazole reagent serving to replace the group $W^1$ with an $R^4$ group of formula (c-1); or
c) reacting a compound of formula (IV):

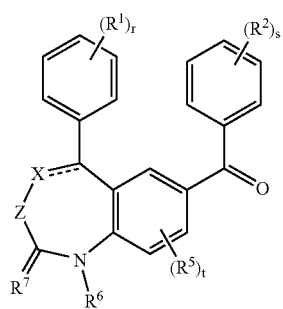

with an imidazole reagent to form a compound of formula (I) in which $R^4$ is a group of formula (c-2), or with a 3-mercapto-4-$C_{1-6}$alkyl-1,2,4-triazole reagent to form the corresponding 3-mercapto-4-$C_{1-6}$alkyl-1,2,4-triazole derivative, which is optionally methylated to form the corresponding 3-methylmercapto derivative, and subsequently removing the 3-mercapto or 3-methylmercapto group to form a compound of formula (I) in which $R^4$ is a group of formula (c-3) in which $R^{18}$ is a $C_{1-6}$alkyl group; or with a 3-bromopyridyl reagent to form a compound of formula (I) wherein $R^4$ is a group of formula (c4);

and optionally effecting one or more of the following conversions in any desired order:
(i) converting a compound of formula (I) into a different compound of formula (I);
(ii) converting a compound of formula (I) in to a pharmaceutically acceptable salt or N-oxide thereof;
(iii) converting a pharmaceutically acceptable salt or N-oxide of a compound of formula (I) into the parent compound of formula (I);
(iv) preparing a stereochemical isomeric form of a compound of formula (I) or a pharmaceutically acceptable salt or N-oxide thereof.

9. A compound according to claim 2 in which:
Z is $C_{1-2}$ alkanediyl,
r is 0, 1 or 2;
s is 0 or 1;
t is 0;
$R^1$ is halo, $C_{1-6}$alkyl, $C_{2-6}$alkenyl, $C_{2-6}$alkynyl or two $R^1$ substituents ortho to one another on the phenyl ring may independently form together a bivalent radical of formula (a-1);
$R^2$ is halo, cyano, nitro, CHO, —$CR^{24}$=N—$OR^{25}$ in which $R^{24}$ is hydrogen and $R^{25}$ is hydrogen or $C_{1-6}$alkyl, or two $R^2$ substituents ortho to one another on the phenyl ring may independently form together a bivalent radical of formula (a-1);
$R^3$ is $Het^2$ or a group of formula (b-1) or (b-3) wherein $R^{10}$ is hydrogen or a group of formula -Alk-$OR^{13}$.
$R^{11}$ is hydrogen;
$R^{12}$ is hydrogen, $C_{1-6}$alkyl, $C_{1-6}$alkylcarbonyl, hydroxy, $C_{1-6}$alkyloxy or mono- or di($C_{1-6}$alkyl) amino$C_{1-6}$alkylcarbonyl;
Alk is $C_{1-6}$alkanediyl and $R^{13}$ is hydrogen;
$R^4$ is a group of formula (c-2) or (c-3) wherein
$R^{16}$ is hydrogen, halo or $C_{1-6}$alkyl;
$R^{17}$ is hydrogen or $C_{1-6}$alkyl;
$R^{18}$ is hydrogen or $C_{1-6}$alkyl;
$R^{18a}$ is hydrogen;
$R^6$ is hydrogen, —$(CR^{20}R^{21})_p$—$C_{3-10}$cycloalkyl, —$C_{1-6}$alkyl$CO_2R^{24}$, aminocarbonyl$C_{1-6}$alkyl, -Alk-$Ar^2$ or -AlkHet or $C_{1-6}$alkyl;
$R^7$ is oxygen or sulphur; or $R^6$ and $R^7$ together form a trivalent radical of formula (x-1), (x-2), (x-3), (x-4) or (x-9) and
aryl is phenyl.

10. A compound according to claim 2 in which:
Z is $C_{1-2}$ alkanediyl, r is 0 or 1;
s is 1;
t is 0;
$R^1$ is halo, $C_{1-6}$alkyl or forms a bivalent radical of formula (a-1);
$R^2$ is halo, cyano or $C_{1-6}$alkyl;
$R^3$ is hydrogen or a radical of formula (b-1) or (b-3);
$R^{10}$ is hydrogen or -Alk-$OR^{13}$;
$R^{11}$ is hydrogen;
$R^{12}$ is hydrogen or $C_{1-6}$alkylcarbonyl;
$R^{13}$ is hydrogen;
$R^4$ is a radical of formula (c-2) or (c-3);
$R^{16}$ is hydrogen;
$R^{17}$ is $C_{1-6}$alkyl;
$R^{18}$ is $C_{1-6}$alkyl;
$R^{18a}$ is hydrogen;

R$^6$ is hydrogen, C$_{1-6}$alkyl, —CH$_2$—C$_{3-10}$cycloalkyl, —C$_{1-6}$alkylCO$_2$R$^{24}$ (wherein R$^{24}$ is H, or ethyl), aminocarbonylC$_{1-6}$alkyl, -Alk-Ar$^2$ or -AlkHet$^2$; and R$^7$ is oxygen or sulphur; or R$^6$ and R$^7$ together form a trivalent radical of formula (x-2), (x-3) or (x-4).

11. A compound according to claim 3 in which:

Z is C$_{1-2}$ alkanediyl, r is 0 or 1;

s is 1;

t is 0;

R$^1$ is halo, C$_{1-6}$alkyl or forms a bivalent radical of formula (a-1);

R$^2$ is halo, cyano or C$_{1-6}$alkyl;

R$^3$ is hydrogen or a radical of formula (b-1) or (b-3);

R$^{10}$ is hydrogen or -Alk-OR$^{13}$;

R$^{11}$ is hydrogen;

R$^{12}$ is hydrogen or C$_{1-6}$alkylcarbonyl;

R$^{13}$ is hydrogen;

R$^4$ is a radical of formula (c-2) or (c-3);

R$^{16}$ is hydrogen;

R$^{17}$ is C$_{1-6}$alkyl;

R$^{18}$ is C$_{1-6}$alkyl;

R$^{18a}$ is hydrogen;

R$^6$ is hydrogen, C$_{1-6}$alkyl, —CH$_2$—C$_{3-10}$cycloalkyl, —C$_{1-6}$alkylCO$_2$R$^{24}$ (wherein R$^{24}$ is H, or ethyl), aminocarbonylC$_{1-6}$alkyl, -Alk-Ar$^2$ or -AlkHet$^2$; and R$^7$ is oxygen or sulphur; or R$^6$ and R$^7$ together form a trivalent radical of formula (x-2), (x-3) or (x-4).

12. A compound according to claim 9 in which:

Z is C$_{1-2}$ alkanediyl, r is 0 or 1;

s is 1;

t is 0;

R$^1$ is halo, C$_{1-6}$alkyl or forms a bivalent radical of formula (a-1);

R$^2$ is halo, cyano or C$_{1-6}$alkyl;

R$^3$ is hydrogen or a radical of formula (b-1) or (b-3);

R$^{10}$ is hydrogen or -Alk-OR$^{13}$

R$^{11}$ is hydrogen;

R$^{12}$ is hydrogen or C$_{1-6}$alkylcarbonyl;

R$^{13}$ is hydrogen;

R$^4$ is a radical of formula (c-2) or (c-3);

R$^{16}$ is hydrogen;

R$^{17}$ is C$_{1-6}$alkyl;

R$^{18}$ is C$_{1-6}$alkyl;

R$^{18a}$ is hydrogen;

R$^6$ is hydrogen, C$_{1-6}$alkyl, —CH$_2$—C$_{3-10}$cycloalkyl, —C$_{1-6}$alkylCO$_2$R$^{24}$ (wherein R$^{24}$ is H, or ethyl), aminocarbonylC$_{1-6}$alkyl, -Alk-Ar$^2$ or -AlkHet$^2$; and R$^7$ is oxygen or sulphur; or R$^6$ and R$^7$ together form a trivalent radical of formula (x-2), (x-3) or (x-4).

13. A compound according to claim 2 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (b-3), R$^9$ is hydrogen, R$^{10}$ is hydrogen, R$^{11}$ is hydrogen, R$^{12}$ is hydrogen, R$^4$ is a radical of formula (c-2) or (c-3), R$^{16}$ is hydrogen, R$^{17}$ is C$_{1-6}$alkyl, R$^{18}$ is C$_{1-6}$alkyl, R$^{18a}$ is hydrogen, R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

14. A compound according to claim 3 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (-3), R$^9$ is hydrogen, R$^{10}$ is hydrogen, R$^{11}$ is hydrogen, R$^{12}$ is hydrogen, R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen, R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

15. A compound according to claim 9 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (b-3), R$^9$ is hydrogen, R$^{10}$ is hydrogen, R$^{11}$ is hydrogen, R$^{12}$ is hydrogen, R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen, R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

16. A compound according to claim 4 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (-3), R$^9$ is hydrogen, R$^{10}$ is hydrogen, R$^{11}$ is hydrogen, R$^{12}$ is hydrogen, R$^4$ is a radical of formula (c-2) or (c-3), R$^{16}$ is hydrogen, R$^{17}$ is C$_{1-6}$alkyl, R$^{18}$ is C$_{1-6}$alkyl, R$^{18a}$ is hydrogen, R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

17. A compound according to claim 10 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (b-3), R$^9$ is hydrogen, R$^{10}$ is hydrogen, R$^{11}$ is hydrogen, R$^{12}$ is hydrogen, R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen; R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

18. A compound according to claim 11 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (-3), R$^9$ is hydrogen, R$^{10}$ is hydrogen, R$^{11}$ is hydrogen, R$^{12}$ is hydrogen, R$^4$ is a radical of formula (c-2) or (c-3), wherein R$^{16}$ is hydrogen, R$^{17}$ is C$_{1-6}$alkyl, R$^{18}$ is C$_{1-6}$alkyl, R$^{18a}$ is hydrogen; R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

19. A compound according to claim 12 in which: Z is C$_{1-2}$ alkanediyl, r is 0 or 1, s is 1, t is 0, R$^1$ is halo R$^2$ is halo or cyano, R$^3$ is hydrogen or a radical of formula (b-1) or (-3), R$^9$ is hydrogen, R$^{10}$ is hydrogen, R$^{11}$ is hydrogen, R$^{12}$ is hydrogen, R$^4$ is a radical of formula (c-2) or (c-3), R$^{16}$ is hydrogen, R$^{17}$ is C$_{1-6}$alkyl, R$^{18}$ is C$_{1-6}$alkyl, R$^{18a}$ is hydrogen; R$^6$ is hydrogen, C$_{1-6}$alkyl, —CH$_2$—C$_{3-10}$cycloalkyl or-C$_{1-6}$alkylAr$^2$, and R$^7$ is oxygen or sulphur, or R$^6$ and R$^7$ together form a trivalent radical of formula (x-2) or (x-4).

20. A compound according to claim 2 in which: X is —S—, Z is —CH$_2$—, r and s are 1, t is 0, R$^1$ is halo, R$^2$ is halo or cyano, R$^3$ is a radical of formula (b-1) or (b-3), R$^9$ is hydrogen, R$^{10}$ and R$^{11}$ are hydrogen and R$^{12}$ is hydrogen, R$^4$ is a radical of formula (c-2) or (c-3), R$^{16}$ is hydrogen, R$^{17}$ is C$_{1-6}$alkyl, R$^{18}$ is C$_{1-6}$alkyl, R$^{18a}$ is hydrogen, R$^6$ is hydrogen, C$_{1-6}$alkyl, —CH$_2$—C$_{3-10}$cycloalkyl or -alkylAr$^2$ and R$^7$ is oxygen or sulphur, or R$^6$ and R$^7$ together form a trivalent radical of formula (x-4).

21. A compound according to claim 3 in which: X is —S—, Z is —CH$_2$—, r and s are 1, t is 0, R$^1$ is halo, R$^2$ is halo or cyano, R$^3$ is a radical of formula (b-1) or (b-3), R$^9$ is hydrogen, R$^{10}$ and R$^{11}$ are hydrogen and R$^{12}$ is hydrogen, R$^4$ is a radical of formula (c-2) or (c-3), R$^{16}$ is hydrogen, R$^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^6$ and $R^7$ together form a trivalent radical of formula (x-4).

22. A compound according to claim 9 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen and $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^6$ and $R^7$ together form a trivalent radical of formula (x-4).

23. A compound according to claim 4 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^8$ and $R^7$ together form a trivalent radical of formula (x-4).

24. A compound according to claim 10 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^8$ and $R^7$ together form a trivalent radical of formula (x-4).

25. A compound according to claim 11 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen and $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^6$ and $R^7$ together form a trivalent radical of formula (x-4).

26. A compound according to claim 12 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and $R^7$ is oxygen or sulphur, or $R^8$ and $R^7$ together form a trivalent radical of formula (x-4).

27. A compound according to claim 12 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen and $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^8$ and $R^7$ together form a trivalent radical of formula (x-4).

28. A compound according to claim 13 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur; or $R^8$ and $R^7$ together form a trivalent radical of formula (x-4).

29. A compound according to claim 14 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^6$ and $R^7$ together form a trivalent radical of formula (x-4).

30. A compound according to claim 15 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^6$ and $R^7$ together form a trivalent radical of formula (x-4).

31. A compound according to claim 16 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^6$ and $R^7$ together form a trivalent radical of formula (x-4).

32. A compound according to claim 17 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen and, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^8$ and $R^7$ together form a trivalent radical of formula (x-4).

33. A compound according to claim 18 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and, $R^7$ is oxygen or sulphur, or $R^8$ and $R^7$ together form a trivalent radical of formula (x-4).

34. A compound according to claim 19 in which: X is —S—, Z is —$CH_2$—, r and s are 1, t is 0, $R^1$ is halo, $R^2$ is halo or cyano, $R^3$ is a radical of formula (b-1) or (b-3), $R^9$ is hydrogen, $R^{10}$ and $R^{11}$ are hydrogen, $R^{12}$ is hydrogen, $R^4$ is a radical of formula (c-2) or (c-3), $R^{16}$ is hydrogen, $R^{17}$ is $C_{1-6}$alkyl, $R^{18}$ is $C_{1-6}$alkyl, $R^{18a}$ is hydrogen, $R^6$ is hydrogen, $C_{1-6}$alkyl, —$CH_2$—$C_{3-10}$cycloalkyl or -alkyl$Ar^2$ and $R^7$ is oxygen or sulphur, or $R^6$ and $R^7$ together form a trivalent radical of formula (x-4).

35. A pharmaceutical composition comprising a pharmaceutically acceptable carrier, and an active ingredient comprising a therapeutically effective amount of a compound of claim 1.

36. A pharmaceutical composition comprising a pharmaceutically acceptable carrier, and an active ingredient comprising a therapeutically effective amount of a compound of claim 7.

\* \* \* \* \*